(12) United States Patent
Brown et al.

(10) Patent No.: US 12,274,700 B1
(45) Date of Patent: Apr. 15, 2025

(54) METHODS OF TREATING SYMPTOMS OF CORONAVIRUS INFECTION WITH RNA POLYMERASE INHIBITORS

(71) Applicant: Accencio LLC, Philadelphia, PA (US)

(72) Inventors: Kevin Brown, Philadelphia, PA (US); Kevin Brogle, Philadelphia, NJ (US)

(73) Assignee: ACCENCIO LLC, Philadelphia, PA (US)

(*) Notice: Subject to any disclaimer, the term of this patent is extended or adjusted under 35 U.S.C. 154(b) by 0 days.

(21) Appl. No.: 17/516,283

(22) Filed: Nov. 1, 2021

Related U.S. Application Data

(60) Provisional application No. 63/107,620, filed on Oct. 30, 2020.

(51) Int. Cl.
*A61K 31/506* (2006.01)
*A61K 31/513* (2006.01)
*A61K 45/06* (2006.01)

(52) U.S. Cl.
CPC .......... *A61K 31/506* (2013.01); *A61K 31/513* (2013.01); *A61K 45/06* (2013.01)

(58) Field of Classification Search
CPC ............................. A61K 31/506; A61K 31/513
USPC ....................................................... 514/269
See application file for complete search history.

(56) References Cited

U.S. PATENT DOCUMENTS

| | | | |
|---|---|---|---|
| 10,013,467 B1 | 7/2018 | Brogle | |
| 10,372,713 B1 | 8/2019 | Blake et al. | |
| 2005/0080053 A1 | 4/2005 | Babu et al. | |
| 2007/0053878 A1* | 3/2007 | Haagmans | A61K 39/215 |
| | | | 435/235.1 |
| 2008/0292588 A1 | 11/2008 | Zhou et al. | |
| 2009/0233972 A1 | 9/2009 | Or et al. | |
| 2010/0074863 A1 | 3/2010 | Bhat et al. | |
| 2013/0143835 A1 | 6/2013 | Eneroth et al. | |

FOREIGN PATENT DOCUMENTS

| | | |
|---|---|---|
| CN | 110655546 A | 1/2020 |
| EP | 2166016 A1 | 3/2010 |
| WO | 2000006529 A1 | 2/2000 |
| WO | 2001047883 A1 | 7/2001 |
| WO | 02051425 A1 | 7/2002 |
| WO | 02057287 A2 | 7/2002 |
| WO | 2003000713 A1 | 1/2003 |
| WO | 2003062255 A2 | 7/2003 |
| WO | 2003087298 A2 | 10/2003 |
| WO | 2003093290 A2 | 11/2003 |
| WO | 2003099824 A1 | 12/2003 |
| WO | 2003101993 A1 | 12/2003 |
| WO | 2004000858 A2 | 12/2003 |
| WO | 2004002999 A2 | 1/2004 |
| WO | 2004003138 A2 | 1/2004 |
| WO | 2004007512 A2 | 1/2004 |
| WO | 2004041201 A1 | 5/2004 |
| WO | 2004046159 A1 | 6/2004 |
| WO | 2004052885 A1 | 6/2004 |
| WO | 2004106350 A1 | 12/2004 |
| WO | 2005014543 A1 | 2/2005 |
| WO | 2005084315 A2 | 9/2005 |
| WO | 2006018725 A1 | 2/2006 |
| WO | 2006020082 A1 | 2/2006 |
| WO | 2006021341 A1 | 3/2006 |
| WO | 2006045613 A1 | 5/2006 |
| WO | 2006072347 A2 | 7/2006 |
| WO | 2006116557 A1 | 11/2006 |
| WO | 2006121468 A1 | 11/2006 |
| WO | 2006137953 A1 | 12/2006 |
| WO | 2007039142 A1 | 4/2007 |
| WO | 2007039144 A1 | 4/2007 |
| WO | 2007054741 A1 | 5/2007 |
| WO | 2007136982 A1 | 11/2007 |
| WO | 2006002231 A1 | 1/2008 |
| WO | 2008005542 A2 | 1/2008 |
| WO | 2008043704 A1 | 4/2008 |
| WO | 2008056264 A2 | 5/2008 |
| WO | 2008062206 A2 | 5/2008 |
| WO | 2008082601 A2 | 7/2008 |
| WO | 2008100447 A2 | 8/2008 |
| WO | 2008111978 A1 | 9/2008 |
| WO | 2008112473 A1 | 9/2008 |
| WO | 2008112841 A1 | 9/2008 |
| WO | 2008112848 A1 | 9/2008 |
| WO | 2008112851 A1 | 9/2008 |
| WO | 2008112863 A1 | 9/2008 |
| WO | 2008121634 A2 | 10/2008 |
| WO | 2008124450 A1 | 10/2008 |
| WO | 2009/006740 A1 | 1/2009 |
| WO | 2009005676 A2 | 1/2009 |
| WO | 2009035788 A1 | 3/2009 |
| WO | 2009039127 A1 | 3/2009 |
| WO | 2009039134 A1 | 3/2009 |
| WO | 2009039135 A1 | 3/2009 |

(Continued)

*Primary Examiner* — Raymond J Henley, III

(74) *Attorney, Agent, or Firm* — Leason Ellis LLP

(57) ABSTRACT

A method of treating or alleviating at least one symptom of a coronavirus infection in a subject, by administering to the subject a therapeutically effective amount of an RNA polymerase inhibitor. In some embodiments, the symptom is selected from the group consisting of fever, cough, tiredness, sore throat, diarrhea, conjunctivitis, headache, loss of taste, loss of smell, rash, difficulty breathing, shortness of breath, chest pain, chest pressure, Acute Respiratory Distress Syndrome (ARDS) and organ failure.

15 Claims, No Drawings

(56) References Cited

FOREIGN PATENT DOCUMENTS

| | | |
|---|---|---|
| WO | 2009039246 A2 | 3/2009 |
| WO | 2009046383 A1 | 4/2009 |
| WO | 2009067108 A1 | 5/2009 |
| WO | 2009067392 A1 | 5/2009 |
| WO | 2009067409 A1 | 5/2009 |
| WO | 2009111501 A1 | 9/2009 |
| WO | 2009132123 A1 | 10/2009 |
| WO | 2009137493 A1 | 11/2009 |
| WO | 2009137500 A1 | 11/2009 |
| WO | 2009152095 A2 | 12/2009 |
| WO | 2009152166 A1 | 12/2009 |
| WO | 2010003658 A1 | 1/2010 |
| WO | 2010042830 A1 | 4/2010 |
| WO | 2010075517 A2 | 7/2010 |
| WO | 2010075549 A2 | 7/2010 |
| WO | 2010081082 A2 | 7/2010 |
| WO | 2010084115 A2 | 7/2010 |
| WO | 2010091409 A1 | 8/2010 |
| WO | 2010132538 A1 | 11/2010 |
| WO | 2010135569 A1 | 11/2010 |
| WO | 2011035231 A1 | 3/2011 |
| WO | 2011039221 A2 | 4/2011 |
| WO | 2011092158 A1 | 8/2011 |
| WO | 2011103063 A1 | 8/2011 |
| WO | 2011106929 A1 | 9/2011 |
| WO | 2011112429 A1 | 9/2011 |
| WO | 2011130557 A2 | 10/2011 |
| WO | 2011153588 A1 | 12/2011 |
| WO | 2012018534 A2 | 2/2012 |
| WO | 2012040126 A1 | 3/2012 |
| WO | 2012040127 A1 | 3/2012 |
| WO | 2012058125 A1 | 5/2012 |
| WO | 2012067663 A1 | 5/2012 |
| WO | 2012075140 A1 | 6/2012 |
| WO | 2012088155 A1 | 6/2012 |
| WO | 2012092484 A2 | 7/2012 |
| WO | 2012142075 A1 | 10/2012 |
| WO | 2012142085 A1 | 10/2012 |
| WO | 2012142093 A2 | 10/2012 |
| WO | 2012158271 A1 | 11/2012 |
| WO | 2013009735 A1 | 1/2013 |
| WO | 2013009737 A1 | 1/2013 |
| WO | 2013070887 A1 | 5/2013 |
| WO | 2013096680 A1 | 5/2013 |
| WO | 2013096679 A1 | 6/2013 |
| WO | 2013158746 A1 | 10/2013 |
| WO | 2013163466 A1 | 10/2013 |
| WO | 2013173488 A1 | 11/2013 |
| WO | 2013173492 A1 | 11/2013 |
| WO | 2013187696 A1 | 12/2013 |
| WO | 2014059901 A1 | 4/2014 |
| WO | 2014062596 A1 | 4/2014 |
| WO | 2014078463 A1 | 5/2014 |
| WO | 2014078778 A2 | 5/2014 |
| WO | 2014100498 A1 | 6/2014 |
| WO | 2014100505 A1 | 6/2014 |
| WO | 2014209983 A1 | 12/2014 |
| WO | 2015017713 A1 | 2/2015 |
| WO | 2015034420 A1 | 3/2015 |
| WO | 2015054465 A1 | 4/2015 |
| WO | 2015081297 A1 | 6/2015 |
| WO | 2015095419 A1 | 6/2015 |
| WO | 2015120237 A2 | 8/2015 |
| WO | 2015197028 A1 | 12/2015 |
| WO | 2016049415 A1 | 3/2016 |
| WO | 2016069975 A1 | 5/2016 |
| WO | 2016100569 A1 | 6/2016 |
| WO | 2018048937 A1 | 7/2016 |
| WO | 2016133948 A1 | 8/2016 |
| WO | 2016141890 A1 | 9/2016 |
| WO | 2016144918 A1 | 9/2016 |
| WO | 2016145142 A1 | 9/2016 |
| WO | 2016154241 A1 | 9/2016 |
| WO | 2017040766 A1 | 3/2017 |
| WO | 2017097234 A1 | 6/2017 |
| WO | 2017106710 A1 | 6/2017 |
| WO | 2017223012 A1 | 12/2017 |
| WO | 2017223020 A1 | 12/2017 |
| WO | 2018013937 A1 | 1/2018 |
| WO | 2018031818 A2 | 2/2018 |
| WO | 2018041091 A1 | 3/2018 |
| WO | 2018091542 A1 | 5/2018 |
| WO | 2018127096 A1 | 7/2018 |
| WO | 2018157830 A1 | 9/2018 |
| WO | 2019053696 A1 | 3/2019 |

\* cited by examiner

METHODS OF TREATING SYMPTOMS OF CORONAVIRUS INFECTION WITH RNA POLYMERASE INHIBITORS

CROSS REFERENCE TO RELATED APPLICATION

The present application claims the benefit of U.S. patent application Ser. No. 63/107,620, filed Oct. 30, 2020, which is hereby incorporated by reference in its entirety.

FIELD

The present disclosure relates to methods of treating symptoms of a coronavirus infection, e.g., SARS-COV-19, by administering an RNA polymerase inhibitor.

BACKGROUND

The novel virus 2019-nCOV (SARS-COV-19, COVID-19), is the third well-known coronavirus to cross species to infect human populations in the past two decades. The previous two are the severe acute respiratory syndrome coronavirus (SARS-COV) outbreak in 2002 and the Middle East respiratory syndrome coronavirus (MERS-COV) outbreak in 2012. Like SARS-COV and MERs-CoV, SARS-COV-19 causes severe respiratory illness, and is highly transmissible from human-to-human. On Mar. 11, 2020, the World Health Organization (WHO) declared SARS-COV-19 a global pandemic. Since then, over 20 million people have been infected, and over 750,000 people have died worldwide from the virus. In the United States alone there have been over 5 million infections to date, with over 160,000 deaths.

Most of the critically ill patients do not develop severe clinical manifestations in early stages of the diseases; however, these patients rapidly deteriorate in the later stages of the disease, presenting with Acute Respiratory Distress Syndrome (ARDS) and multiple-organ failure, resulting in death within a short time. Evidence suggests that proinflammatory responses play a role in the pathogenesis of SARS-COV-19 and other coronaviruses. Dysregulations of cytokine-chemokine responses cause the immune system to become hyperactive and induce a condition called a cytokine storm, which is considered to be one of the major causes of ARDS and multiple-organ failure in these patients. Targeting cytokines during the management of SARS-COV-19 patients could improve survival rates and reduce mortality.

To date, no treatment or vaccine has been approved to combat SARS-COV-19. There is therefore an urgent and unmet need for effective means to combat the symptoms of SARS-CoV-19 and other coronaviruses such as SARS-COV and MERS-COV.

SUMMARY

The present disclosure relates to methods of treating one or more symptoms of a coronavirus infection, particularly SARS-COV-19. The present disclosure further relates to methods of treating or preventing an acute inflammatory response, e.g., a cytokine storm in a coronavirus patient, by administering an RNA polymerase inhibitor, in particular a viral polymerase inhibitor.

Broadly, RNA Polymerase (RNAP) is the enzyme that transcribes genetic information from DNA into RNA, which, in turn, directs the assembly of proteins that carry out most biological functions and are key structural components of cells. RNA protease inhibitors prevent viral replication by selectively binding to RNA polymerases and blocking proteolytic cleavage of protein precursors that are necessary for the production of transcription and replication proteins. The present disclosure is based on the discovery that RNA polymerase inhibitors may have therapeutic utility in the treatment of coronavirus symptoms, in particular in reducing inflammation and preventing cytokine storms in patients with coronavirus infections, in particular SARS-COV-19.

Thus, in some embodiments, the present disclosure relates to a method of treating or alleviating at least one symptom of a coronavirus infection in a subject, by administering to the subject a therapeutically effective amount of an RNA polymerase inhibitor. In some embodiments, the symptom is selected from the group consisting of fever, cough, tiredness, sore throat, diarrhea, conjunctivitis, headache, loss of taste, loss of smell, rash, difficulty breathing, shortness of breath, chest pain, chest pressure, Acute Respiratory Distress Syndrome (ARDS) and organ failure. In some embodiments, the subject is a human.

In some embodiments, the present disclosure relates to a method of treating an acute inflammatory condition in a subject infected with a coronavirus, the method comprising the step of administering to the subject a therapeutically effective amount of an RNA polymerase inhibitor. In some embodiments, the inflammatory condition comprises a cytokine storm. In some embodiments, the subject is a human.

In some embodiments, the present disclosure relates to a method of preventing a cytokine storm in a subject infected with a coronavirus, the method comprising the step of administering to the subject a therapeutically effective amount of an RNA polymerase inhibitor. In some embodiments, the subject is a human.

In some embodiments, the present disclosure relates to a method of reducing or arresting viral load in a subject infected with a coronavirus, the method comprising the step of administering to the subject a therapeutically effective amount of an RNA polymerase inhibitor. In some embodiments, the subject is a human.

In some embodiments, the coronavirus is a severe acute respiratory syndrome coronavirus (SARS-COV). In some embodiments, the coronavirus is a novel virus 2019-nCOV (SARS-COV-19). In some embodiments, the coronavirus is a Middle East respiratory syndrome coronavirus (MERS-CoV). In one preferred embodiment, the coronavirus is SARS-COV-19. In some embodiments, the RNA polymerase inhibitor is ((2R,3S,4S,5R)-2-(4-amino-2-oxopyrimidin-1-yl)-4-hydroxy-5-(hydroxymethyl)oxolane-3-carbonitrile); 1-[(2R,3R,4S,5R)-3,4-dihydroxy-5-(hydroxymethyl)oxolan-2-yl]pyrimidine-2,4-dione; [(2R,3R,5R)-5-(4-amino-2-oxopyrimidin-1-yl)-4,4-difluoro-3-hydroxyoxolan-2-yl]methyl (E)-octadec-9-enoate; and (1-(3-C-Ethynyl-beta-D-ribo-pentofuranosyl) cytosine) or variations, combinations or salts thereof. Combinations of RNA polymerase inhibitors may also be used in the methods of the present disclosure.

In some embodiments, the RNA polymerase inhibitors are selected from the group consisting of a compound of any one of Table 1.

In some embodiments, RNA polymerase inhibitor is administered according to a dose regimen selected from the group consisting of once daily (q.d.), twice daily (b.i.d.) thrice daily (t.i.d.), once a week, twice a week, three times a week, once every 2 weeks, once every three weeks, or once a month.

In some embodiments, the RNA polymerase inhibitor is administered in a pharmaceutical composition, wherein the composition further comprises at least one pharmaceutically acceptable excipient.

In some embodiments, the RNA polymerase inhibitor is administered in a form selected from the group consisting of a solution, a suspension, a syrup, an emulsion, a dispersion, a tablet, a pill, a capsule, a pellet, granules, a powder, an ointment, an elixir, a wafer, coated or uncoated beads, a lozenge, a sachet, a cachet, a depot system, a patch, an aerosol, an oil, an ointment, a suppository, a gel, and a cream.

In some embodiments, the pharmaceutical composition is formulated for oral, topical, mucosal, intranasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural, sublingual oral, intranasal, intravenous, intraarterial, intrathecal, vaginal, rectal or subcutaneous administration.

In some embodiments, the present disclosure relates to a topical pharmaceutical composition in a form selected from the group consisting of ointment, a gel, a drop, a patch and a cream, the composition comprising an RNA polymerase inhibitor and at least one topically acceptable excipient, wherein the RNA polymerase inhibitor is selected from the group consisting of the compounds provided in Table 1.

Further embodiments and the full scope of applicability of the present disclosure will become apparent from the detailed description given hereinafter. However, it should be understood that the detailed description and specific examples, while indicating preferred embodiments of the disclosure, are given by way of illustration only, since various changes and modifications within the spirit and scope of the present disclosure will become apparent to those skilled in the art from this detailed description.

DETAILED DESCRIPTION

As used herein and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

As used herein and as well understood in the art, the term an "effective amount," "sufficient amount" or "therapeutically effective amount" of an agent as used herein interchangeably, is that amount sufficient to effectuate beneficial or desired results, including preclinical and/or clinical results and, as such, an "effective amount" or its variants depends upon the context in which it is being applied. The response is in some embodiments preventative, in others therapeutic, and in others a combination thereof. The term "effective amount" also includes the amount of a compound of the disclosure, which is "therapeutically effective" and which avoids or substantially attenuates undesirable side effects.

As used herein and as well known in the art, and unless otherwise defined, the term "subject" means an animal, including but not limited a human, monkey, cow, horse, sheep, pig, chicken, turkey, quail, cat, dog, mouse, rat, rabbit, or guinea pig. In one embodiment, the subject is a mammal and in another embodiment the subject is a human coronavirus patient.

Molecular studies have indicated that RNA Polymerase directs the transcription of RNA form nucleic acid templates. in of proteins that carry out most biological functions and are key structural components of cells. Broadly, polymerase inhibitors prevent viral replication by selectively binding to RNA polymerases or the transcription complexes and block the formation of macromolecular structures necessary for the production of infectious viral particles. According to current research, polymerases have utility in preventing the RNA transcription process from being successfully completed, either by interrupting the synthesis process directly or by preventing the formation of the necessary transcription factor complexes. RNA polymerase inhibitors targets these functions from being carried out and preset mechanisms for treating an acute viral infection.

RNA polymerase inhibitors have been developed to treat Human Immunodeficiency Virus (HIV) and hepatitis C. deficiency. Because other viruses also encode for the same RNA polymerases that are essential to viral replication, the present disclosure extends the utility of protease inhibitors for other viruses, such as SARS-COV-19, where the processing site sequence and the catalytic mechanism are known and understood.

For example, a compound for use in the method of the present disclosure is an RNA polymerase inhibitor.

In one implementation, the compound is 2-CdAP or other 2'-substituted-$N^6$-substituted purine nucleotides that have been clinically investigated. In one particular implementation, the compound, or variations and permutations thereof, is described in WO2013096679; WO2015081297; WO2015161137; WO2016115222; WO2018048937 the contents of which are hereby incorporated by reference for all purposes and the specific purposes identified herein In one implementation, the compound is 5-fluoro-2'-deoxycytidine, a Methyltransferase inhibitor under clinical investigation. In one particular implementation, the compound, or variations and permutations thereof, is described in US20040229840; WO02057287; WO2003062255; WO2003093290; WO2004000858; WO2004002999; WO2008121634; WO2009067409; WO2013009737; WO2013070887; WO2013096679; WO2014062596; WO2014100505; WO2014209983; WO2015081297; WO2015095419; WO2015120237; WO2016069975; WO2016069975; WO2016100569; WO2016115222 the contents of which are hereby incorporated by reference for all purposes and the specific purposes identified herein.

In one implementation, the RNA polymerase inhibitor compound is 625433 (HCV polymerase inhibitor) having the formula D-Proline, 1-(4-(1,1-dimethylethyl)-3-methoxybenzoyl)-4-(methoxymethyl)-2-(1H-pyrazol-1-ylmethyl)-5-(2-thiazolyl)-, (4R,5S)-rel-.

In one particular implementation, the compound, or variations and permutations thereof, is described in US20090233972; US20100074863; WO2006045613; WO2007039142; WO2007039144 the contents of which are hereby incorporated by reference for all purposes and the specific purposes identified herein.

In one implementation, the RNA polymerase inhibitor compound is ALS-8112, substituted nucleosides, nucleotides and analogs thereof, such as NS5B polymerase inhibitors having the formula 4-amino-1-[(2R,3R,4R,5R)-5-(chloromethyl)-3-fluoro-4-hydroxy-5-(hydroxymethyl)oxolan-2-yl]pyrimidin-2-one.

In one particular implementation, the compound, or variations and permutations thereof, is described in US20040229840; WO02057287; WO2003062255; WO2003093290; WO2004000858; WO2004002999; WO2008121634; WO2009067409; WO2012142085; WO2013009737; WO2013070887; WO2013096679; WO2014062596; WO2014100505; WO2014209983; WO2015081297; WO2015095419; WO2015120237; WO2016069975; WO2016100569; WO2016115222 the contents of which are hereby incorporated by reference for all purposes and the specific purposes identified herein.

In one implementation, the RNA polymerase inhibitor compound is ARL-67085, or other 3'-substituted methyl or alkynyl nucleoside compounds or 2'-Substituted-N 6-substituted purine nucleotides.

In one particular implementation, the compound, or variations and permutations thereof, is described in WO2015161137; WO2018048937 the contents of which are hereby incorporated by reference for all purposes and the specific purposes identified herein.

In one implementation, the RNA polymerase inhibitor compound is AV-4025, having a formula methyl N-[(2S)-1-[(2S)-2-[5-[4-[4-[2-[(2S)-1-[(2S)-2-(methoxycarbonylamino)-3-methylbutanoyl]pyrrolidin-2-yl]-1H-imidazol-5-yl]buta-1,3-diynyl]phenyl]-1H-imidazol-2-yl]pyrrolidin-1-yl]-3-methyl-1-oxobutan-2-yl]carbamate or another antiviral compound with an imidazole-biphenyl-imidazole core.

In one particular implementation, the compound, or variations and permutations thereof, is described in WO2013173492 the contents of which are hereby incorporated by reference for all purposes and the specific purposes identified herein.

In one implementation, the RNA polymerase inhibitor compound is an adenogesic, such as substituted Adenosine derivatives.

In one particular implementation, the compound, or variations and permutations thereof, is described in WO02057287; WO2003062255; WO2003093290; WO2004000858; WO2004002999; WO2004003138; WO2008062206; WO2009067409; WO2010075517; WO2010075549; WO2010081082; WO2010084115; WO2012092484; WO2012142075; WO2012142093; WO2013070887; WO2013096679; WO2014100498; WO2014209983; WO2015081297; WO2015120237; WO2016069975; WO2016115222; WO2016144918 the contents of which are hereby incorporated by reference for all purposes and the specific purposes identified herein.

In one implementation, the RNA polymerase inhibitor compound is CS-92, or chemical derivatives of 4'-substituted nucleosides (1',3',4'-triacyl pyrimidine nucleoside) such as 4-amino-1-((2R,4S,5S)-4-azido-5-(hydroxymethyl)tetrahydrofuran-2-yl)-5-methylpyrimidin-2 (1H)-one.

In one particular implementation, the compound, or variations and permutations thereof, is described in EP02166016; WO2004046159; WO2006021341; WO2008043704; WO2009067409; and WO2016115222 the contents of which are hereby incorporated by reference for all purposes and the specific purposes identified herein. In some embodiments, such compounds are represented by any one or more of the structures shown in Table 1. Any one of the compounds depicted in Table 1 is suitable for use in the methods of the present disclosure.

TABLE 1

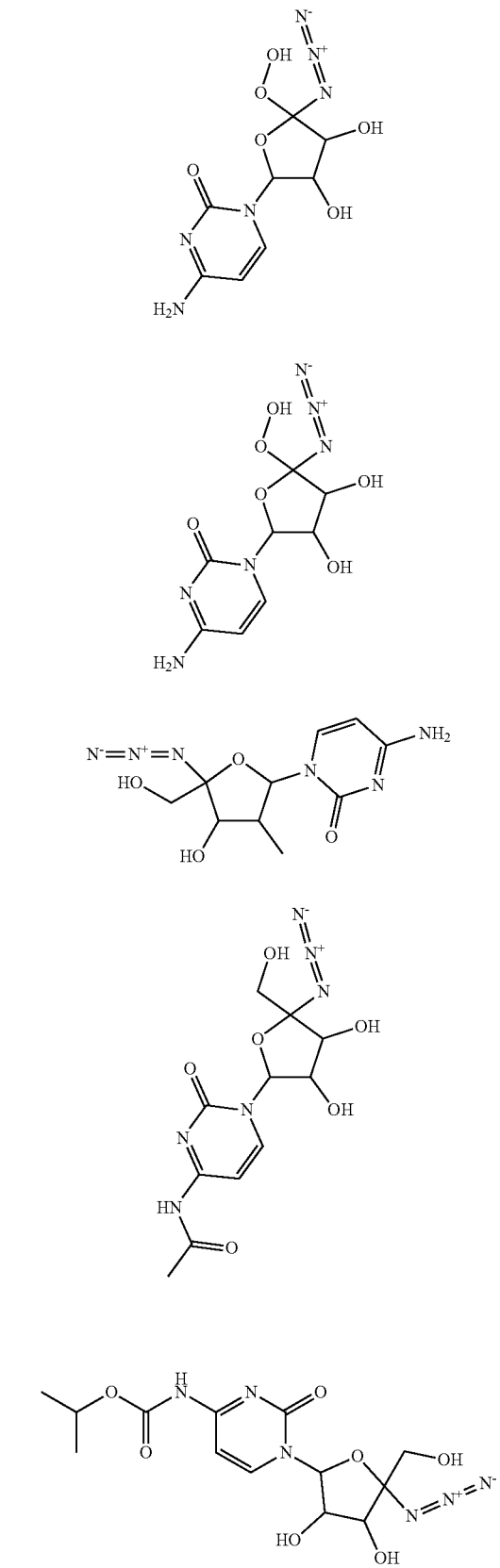

TABLE 1-continued
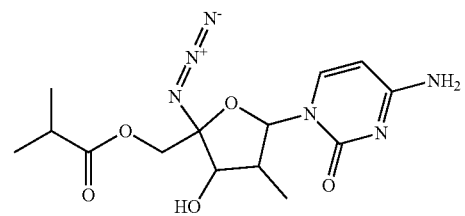 [SMILES: CC(C)C(=O)OCC1(N=[N+]=[N-])OC(n2ccc(N)nc2=O)C(C)C1O]
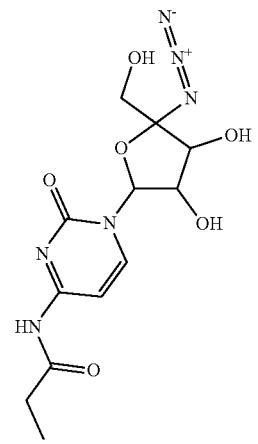 [SMILES: CCC(=O)Nc1ccn(C2OC(CO)(N=[N+]=[N-])C(O)C2O)c(=O)n1]
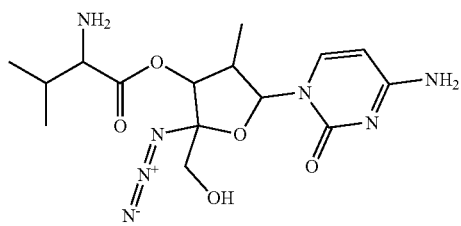 [SMILES: CC(C)C(N)C(=O)OC1C(C)C(n2ccc(N)nc2=O)OC1(CO)N=[N+]=[N-]]
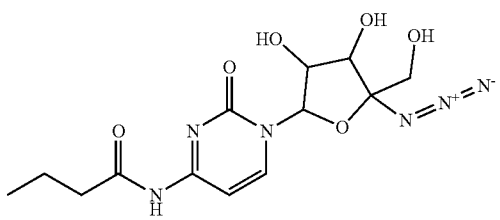 [SMILES: CCCC(=O)Nc1ccn(C2OC(CO)(N=[N+]=[N-])C(O)C2O)c(=O)n1]
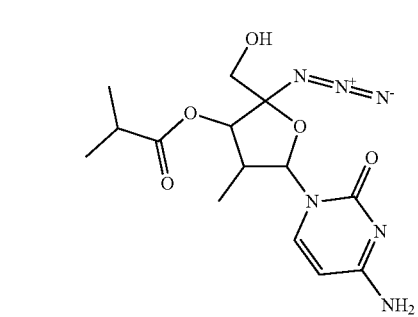 [SMILES: CC(C)C(=O)OC1C(C)C(n2ccc(N)nc2=O)OC1(CO)N=[N+]=[N-]]
TABLE 1-continued
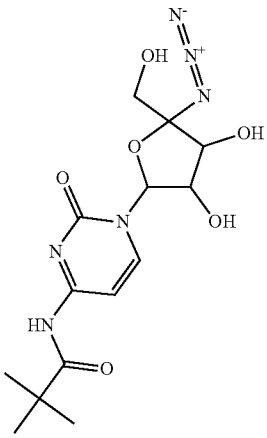 [SMILES: CC(C)(C)C(=O)Nc1ccn(C2OC(CO)(N=[N+]=[N-])C(O)C2O)c(=O)n1]
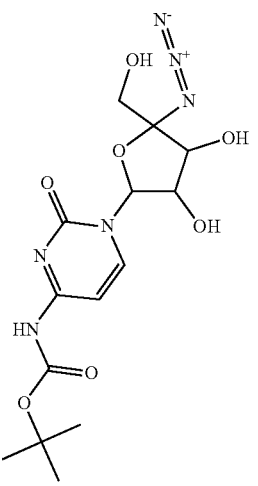 [SMILES: CC(C)(C)OC(=O)Nc1ccn(C2OC(CO)(N=[N+]=[N-])C(O)C2O)c(=O)n1]
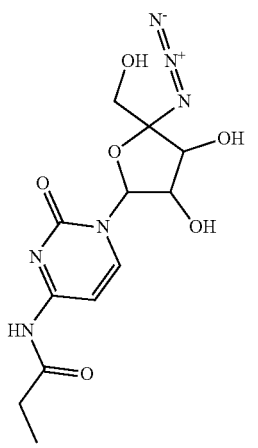 [SMILES: CCC(=O)Nc1ccn(C2OC(CO)(N=[N+]=[N-])C(O)C2O)c(=O)n1]
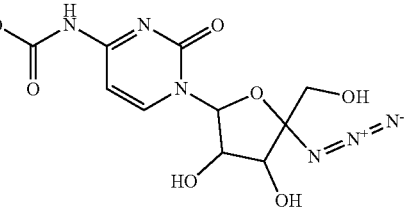

TABLE 1-continued

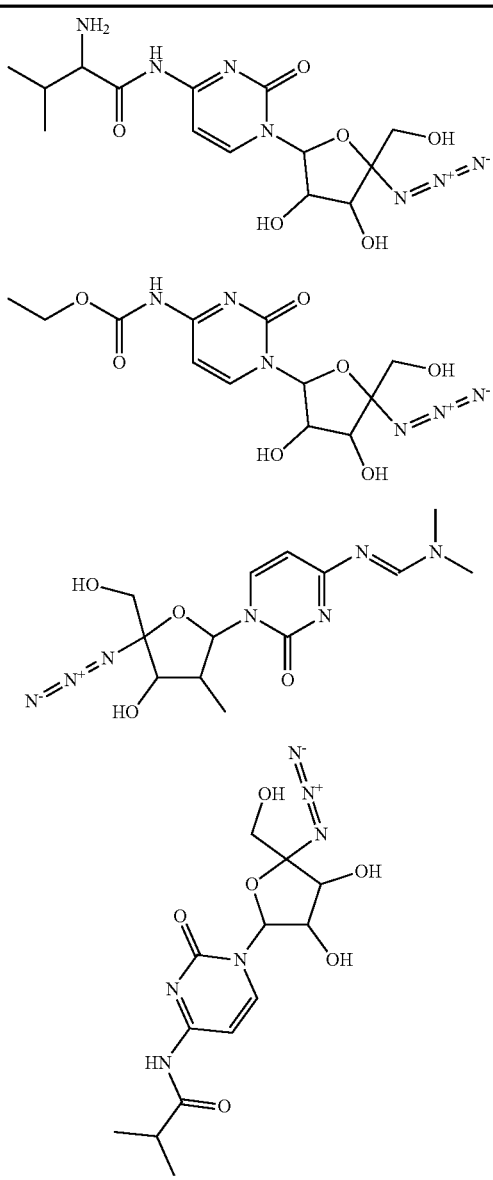

In one implementation, the RNA polymerase inhibitor compound is DFP-10917, TAS-109 or a compound having the formula (2R,3S,4S,5R)-2-(4-amino-2-oxopyrimidin-1-yl)-4-hydroxy-5-(hydroxymethyl)oxolane-3-carbonitrile.

In one particular implementation, the compound, or variations and permutations thereof, is described in WO2009067409 (23), WO2014062596 (2), WO2013096679 (28), WO2016100569 (9), WO2014100505 (4), WO2015120237 (13), WO2014209983 (7), WO2004002999 (1), WO2016069975 (2), US20040229840 (2), WO02057287 (9), WO2003062255 (1), WO2003093290 (2), WO2004000858 (2), WO2012142085 (1), WO2015081297 (1), the contents of which are hereby incorporated by reference for all purposes and the specific purposes identified herein.

In one implementation, the RNA polymerase inhibitor compound is DMDC or Dimethyldicarbonate.

In one particular implementation, the compound, or variations and permutations thereof, is described in WO200906740 and WO2013096679 the contents of which are hereby incorporated by reference for all purposes and the specific purposes identified herein.

In one implementation, the RNA polymerase inhibitor compound is GR-79236 having the formula N-[(1 S, trans)-2-hydroxycyclopentyl] adenosine.

In one particular implementation, the compound, or variations and permutations thereof, is described in WO2003093290; and WO2004002999 the contents of which are hereby incorporated by reference for all purposes and the specific purposes identified herein.

In one implementation, the RNA polymerase inhibitor compound is HCV-371 having the formula [(1R)-5-cyano-8-methyl-1-propyl-1,3,4,9-tetrahydropyano[3,4-b]indol-1-yl]acetic acid.

In one particular implementation, the compound, or variations and permutations thereof, is described in WO2003099824 and WO2005084315 the contents of which are hereby incorporated by reference for all purposes and the specific purposes identified herein.

In one implementation, the RNA polymerase inhibitor compound is LY-2334737 having the formula N-[1-[(2R,4R,5R)-3,3-difluoro-4-hydroxy-5-(hydroxymethyl)oxolan-2-yl]-2-oxopyrimidin-4-yl]-2-propylpentanamide.

In one particular implementation, the compound, or variations and permutations thereof, is described in WO2003093290; WO2004002999; WO2004046159; WO2008043704; WO2009067409; WO2013096679; and WO2014209983 the contents of which are hereby incorporated by reference for all purposes and the specific purposes identified herein.

In one implementation, the RNA polymerase inhibitor compound is MBC-1, MBC-11 or a compound having the formula [1-[[[(2R,3S,4S,5R)-5-(4-amino-2-oxopyrimidin-1-yl)-3,4-dihydroxyoxolan-2-yl]methoxy-hydroxyphosphoryl]oxy-hydroxyphosphoryl]-1-hydroxyethyl]phosphonic acid.

In one particular implementation, the compound, or variations and permutations thereof, is described in US20040229840; WO2008005542; WO2008082601; WO2012142085; WO2012142093; WO2013096679; WO2014062596; WO2014100505; WO2014209983; WO2015034420; WO2015081297; WO2015095419; WO2015161137; WO2016100569; WO2016115222; and WO2017106710 the contents of which are hereby incorporated by reference for all purposes and the specific purposes identified herein.

In one implementation, the RNA polymerase inhibitor compound isln one implementation, the RNA polymerase inhibitor compound is CNDAC (DFP-10917) and deoxycytosine nucleoside analog with antineoplastic activity having the formula (2R,3S,4S,5R)-2-(4-amino-2-oxopyrimidin-1-yl)-4-hydroxy-5-(hydroxymethyl)oxolane-3-carbonitrile.

In one particular implementation, the compound, or variations and permutations thereof, is described in US20040229840; WO02057287; WO2003062255; WO2003093290; WO2004000858; WO2004002999; WO2008121634; WO2009067409; WO2012142085; WO2013009737; WO2013070887; WO2013096679; WO2014062596; WO2014100505; WO2014209983; WO2015081297; WO2015095419; WO2015120237; WO2016069975; WO2016100569; and WO2016115222, the contents of which are hereby incorporated by reference for all purposes and the specific purposes identified herein.

In one implementation, the RNA polymerase inhibitor compound is DMDC or 2',4'-substituted nucleoside derivatives such as 4-amino-1-[(2R,4S,5R)-4-hydroxy-5-(hydroxymethyl)-3-methylideneoxolan-2-yl]pyrimidin-2-one.

In one particular implementation, the compound, or variations and permutations thereof, is described in WO2009067409 the contents of which are hereby incorporated by reference for all purposes and the specific purposes identified herein.

In one implementation, the RNA polymerase inhibitor compound is GR-7936, 2' and 3'-nucleoside produgs.

In one particular implementation, the compound, or variations and permutations thereof, is described in WO2003093290 and WO2004002999 the contents of which are hereby incorporated by reference for all purposes and the specific purposes identified herein.

In one implementation, the RNA polymerase inhibitor compound is HCV-371, a RNA-dependent RNA polymerase (RdRp), of a compound having the formula [(1R)-5-cyano-8-methyl-1-propyl-1,3,4,9-tetrahydropyano[3,4-b]indol-1-yl]acetic acid (HCV-371).

In one particular implementation, the compound, or variations and permutations thereof, is described in WO2003099824 and WO2005084315 the contents of which are hereby incorporated by reference for all purposes and the specific purposes identified herein.

In one implementation, the RNA polymerase inhibitor compound is LY-2334737, or a compound having the formula N-(1-((2S,4R,5R)-3,3-difluoro-4-hydroxy-5-(hydroxymethyl)tetrahydrofuran-2-yl)-2-oxo-1,2-dihydropyrimidin-4-yl)-2-propylpentanamide.

In one particular implementation, the compound, or variations and permutations thereof, is described in the contents of which are WO2003093290; WO2004002999; WO2004046159; WO2008043704; WO2009067409; WO2013096679 and WO2014209983, the contents of which are hereby incorporated by reference for all purposes and the specific purposes identified herein.

In one implementation, the RNA polymerase inhibitor compound is MBC-11 or a compound having the formula (1-((((((2R,3S,4S,5R)-5-(4-amino-2-oxopyrimidin-1(2H)-yl)-3,4-dihydroxytetrahydrofuran-2-yl)methoxy)(hydroxy) phosphoryl)oxy)(hydroxy)phosphoryl)-1-hydroxyethyl) phosphonic acid, or one or more 3'-Substituted methyl or alkynyl nucleosides.

In one particular implementation, the compound, or variations and permutations thereof, is described in US20040229840; WO2008005542; WO2008082601; WO2012142085; WO2012142093; WO2013096679; WO2014062596; WO2014100505; WO2014209983; WO2015034420; WO2015081297; WO2015095419; WO2015161137; WO2016100569; WO2016115222; WO2017106710 the contents of which are hereby incorporated by reference for all purposes and the specific purposes identified herein.

In one implementation, the RNA polymerase inhibitor compound is MK-0608, a nucleoside derivative having the formula $C_{12}H_{16}N_4O_4$ or 9-(2'-C-methyl-3-D-ribofuranosyl)-6-(thiophen-3-yl)-purine.

In one particular implementation, the compound, or variations and permutations thereof, is described in WO02057287; WO2003093290; WO2004007512; WO2006116557; WO20061214681 WO2010084115; WO2012142085; WO2012142093; WO2013009735; WO2016069975 and WO2018031818 the contents of which are hereby incorporated by reference for all purposes and the specific purposes identified herein.

In one implementation, the RNA polymerase inhibitor compound is Mk-3281 having the formula 14-cyclohexyl-7-((2-(dimethylamino)ethyl)(methyl)amino)-7,8-dihydro-6H-benzo[2,3][1,5]oxazocino[5,4-a]indole-11-carboxylic acid.

In one particular implementation, the compound, or variations and permutations thereof, is described in WO2007054741 and WO2006020082 the contents of which are hereby incorporated by reference for all purposes and the specific purposes identified herein.

In one implementation, the RNA polymerase inhibitor compound is MK-8325 having a formula ethyl ((S)-1-((R)-5-(7-(4-(2-((S)-4,4-difluoro-1-((methoxycarbonyl)-L-valyl) pyrrolidin-2-yl)-1H-imidazol-5-yl)phenyl)-1H-naphtho[1, 2-d]imidazol-2-yl)-3,3-dimethyl-1,3-azasilolidin-1-yl)-3-methyl-1-oxobutan-2-yl)carbamate dihydrochloride.

In one particular implementation, the compound, or variations and permutations thereof, is described in WO2011112429 and WO2016141890 the contents of which are hereby incorporated by reference for all purposes and the specific purposes identified herein.

In one implementation, the RNA polymerase inhibitor compound is NPC-15 having a formula (E)-N-(4-tert-butylphenyl)-3 (1H-indol-3-yl) acrylamide or another Melatonin receptor agonist.

In one particular implementation, the compound, or variations and permutations thereof, is described in WO2013187696 the contents of which are hereby incorporated by reference for all purposes and the specific purposes identified herein.

In one implementation, the RNA polymerase inhibitor compound is Nu-3 ([(2R,3S,5R)-3-[butoxy(hydroxy)phosphoryl]oxy-5-(5-methyl-2,4-dioxopyrimidin-1-yl)oxolan-2-yl]methyl butyl hydrogen phosphate) or another 2'-Dichloro and 2'-fluoro-2'-chloro nucleoside analog.

In one particular implementation, the compound, or variations and permutations thereof, is described in CN110655546; WO02057287; WO2012088155; WO201508129 and WO2017106710 the contents of which are hereby incorporated by reference for all purposes and the specific purposes identified herein.

In one implementation, the RNA polymerase inhibitor compound is OTH-719, a clinically investigated 4'-Difluoromethyl substituted nucleoside derivative and or 2'-Methyl substituted nucleoside derivative.

In one particular implementation, the compound, or variations and permutations thereof, is described in WO2014062596 and WO2015120237 the contents of which are hereby incorporated by reference for all purposes and the specific purposes identified herein.

In one implementation, the RNA polymerase inhibitor compound is OVI-123 and or other clinically investigated substituted purine nucleosides, phosphoramidate and phosphordiamidate derivatives.

In one particular implementation, the compound, or variations and permutations thereof, is described in WO02057287; WO2003062255; WO2003093290; WO2004000858; WO2004002999; WO2004003138; WO2008062206; WO2009067409; WO2009067409; WO2010075517; WO2010075549; WO2010081082; WO2012092484; WO2012142093; WO2013070887; WO2013096679; WO2014100498; WO2014209983; WO2015081297; WO2015120237; WO2016069975; WO2016115222 and WO2018031818 the contents of which are hereby incorporated by reference for all purposes and the specific purposes identified herein.

In one implementation, the RNA polymerase inhibitor compound is POL-240 (uridine, Navigen, Repligen) having the formula (1-[(2R,3R,4S,5R)-3,4-dihydroxy-5-(hydroxymethyl)oxolan-2-yl]pyrimidine-2,4-dione) and clinically investigated viral polymerase inhibitor.

In one particular implementation, the compound, or variations and permutations thereof, is described in WO2011153588 and WO2013187696 the contents of which are hereby incorporated by reference for all purposes and the specific purposes identified herein In one implementation, the RNA polymerase inhibitor compound is Pol-255 (1-beta-D-Ribofuranosyluracil) or other 4'-OR nucleosides.

In one particular implementation, the compound, or variations and permutations thereof, is described in CN110655546; US20130143835; WO02051425; WO02057287; WO2004000858; WO2008121634; WO2009067409; WO2011092158; WO2012142085; WO2012142093; WO2013070887; WO2013096679; WO2014062596; WO2014078463; WO2014100505; WO2014209983; WO2015034420; WO2015081297; WO2015095419; WO2015120237; WO2016100569 and WO2016115222 the contents of which are hereby incorporated by reference for all purposes and the specific purposes identified herein.

In one implementation, the RNA polymerase inhibitor compound is PSI-6130 (4-amino-1-((2R,3S,4R,5R)-3-fluoro-4-hydroxy-5-(hydroxymethyl)-3-methyltetrahydrofuran-2-yl)pyrimidin-2(1H)-one).

In one particular implementation, the compound, or variations and permutations thereof, is described in US20040229840; WO02057287; WO2003062255; WO2003093290; WO2004000858; WO2004002999; WO2008121634; WO2009067409; WO2012142085; WO2013009737; WO2013070887; WO2013096679; WO2014062596; WO2014100505; WO2014209983; WO2015081297; WO2015095419; WO2015120237; WO2016069975; WO2016100569 and WO2016115222 the contents of which are hereby incorporated by reference for all purposes and the specific purposes identified herein.

In one implementation, the RNA polymerase inhibitor compound is PSI-938 (4aR,6R,7R,7aR)-6-(2-amino-6-ethoxy-9H-purin-9-yl)-7-fluoro-2-isopropoxy-7-methyltetrahydro-4H-furo[3,2-d][1,3,2]dioxaphosphinine 2-oxide).

In one particular implementation, the compound, or variations and permutations thereof, is described in WO2009152095; WO2012142075; WO2012142085; WO2012142093; WO2014100505; WO2015081297; WO2017223012 the contents of which are hereby incorporated by reference for all purposes and the specific purposes identified herein.

In one implementation, the RNA polymerase inhibitor compound is R-1479 (4-amino-1-((2R,3R,4S,5R)-5-azido-3,4-dihydroxy-5-(hydroxymethyl)tetrahydrofuran-2-yl)pyrimidin-2(1H)-one).

In one particular implementation, the compound, or variations and permutations thereof, is described in EP02166016; WO2003093290; WO2003093290; WO2004002999; WO2004046159; WO2006021341; WO2008043704; WO2009067409; WO2014209983 and WO2016115222 the contents of which are hereby incorporated by reference for all purposes and the specific purposes identified herein.

In one implementation, the RNA polymerase inhibitor compound is R-phenylisopropyladenosine.

In one particular implementation, the compound, or variations and permutations thereof, is described in WO2010081082 and WO2012092484 the contents of which are hereby incorporated by reference for all purposes and the specific purposes identified herein In one implementation, the RNA polymerase inhibitor compound is Ro-09-4889.

In one particular implementation, the compound, or variations and permutations thereof, is described in WO2004046159 and WO2008043704 the contents of which are hereby incorporated by reference for all purposes and the specific purposes identified herein In one implementation, the RNA polymerase inhibitor compound is Ro-31-6840 (4-amino-1-[(2R,3S,5S)-3-fluoro-5-(hydroxymethyl)oxolan-2-yl]pyrimidin-2-one).

In one particular implementation, the compound, or variations and permutations thereof, is described in US20040229840; WO02057287; WO2003062255; WO2003093290; WO2004000858; WO2004002999; WO2008121634; WO2009067409; WO2012142085; WO2013009737; WO2013070887; WO2013096679; WO2014062596; WO2014100505; WO2014100505; WO2014209983; WO2015081297; WO2015095419; WO2015120237; WO2016069975; WO2016100569 and WO2016115222 the contents of which are hereby incorporated by reference for all purposes and the specific purposes identified herein In one implementation, the RNA polymerase inhibitor compound is SDZ-WAG-994 (9-(2'-C-methyl-β-D-ribofuranosyl)-6-(thiophen-3-yl)-purine).

In one particular implementation, the compound, or variations and permutations thereof, is described in WO2003093290 and WO2004002999 the contents of which are hereby incorporated by reference for all purposes and the specific purposes identified herein.

In one implementation, the RNA polymerase inhibitor compound is SHP-622 (3-(1H-indol-3-yl)propanoic acid).

In one particular implementation, the compound, or variations and permutations thereof, is described in WO2011153588 and WO2013187696 the contents of which are hereby incorporated by reference for all purposes and the specific purposes identified herein.

In one implementation, the RNA polymerase inhibitor compound is TMC-647055 (19-Methano-3,7:4,1-dimetheno-1H,11H-14,10,2,9,11,17-benzoxathiatetraazacyclodocosine-8,18(9H,15H)-dione, 27-cyclohexyl-12,13,16,17-tetrahydro-22-methoxy-11,17-dimethyl-, 10,10-dioxide).

In one particular implementation, the compound, or variations and permutations thereof, is described in WO2010003658 the contents of which are hereby incorporated by reference for all purposes and the specific purposes identified herein.

In one implementation, the RNA polymerase inhibitor compound is TMC-649128 ((2R,3S,4S,5R)-5-(4-amino-2-oxopyrimidin-1(2H)-yl)-2-azido-2-((isobutyryloxy)methyl)-4-methyltetrahydrofuran-3-yl isobutyrate).

In one particular implementation, the compound, or variations and permutations thereof, is described in WO2008043704 the contents of which are hereby incorporated by reference for all purposes and the specific purposes identified herein In one implementation, the RNA polymerase inhibitor compound is UFT (5-fluoro-1-(oxolan-2-yl)pyrimidine-2,4-dione; 1H-pyrimidine-2,4-dione) or other Cyclic Nucleotide analogs.

In one particular implementation, the compound, or variations and permutations thereof, is described in WO2012088155 the contents of which are hereby incorporated by reference for all purposes and the specific purposes identified herein.

In one implementation, the RNA polymerase inhibitor compound is VX-135 or another clinically investigated nucleotide analogue HCV polymerase inhibitor.

In one particular implementation, the compound, or variations and permutations thereof, is described in WO2012040127; WO2013096680; WO2014100505; WO2015054465; WO2015081297; WO2015095419 and WO2015161137 the contents of which are hereby incorporated by reference for all purposes and the specific purposes identified herein.

In one implementation, the RNA polymerase inhibitor compound is YT-146 (Adenosine, 2-(1-octynyl)-).

In one particular implementation, the compound, or variations and permutations thereof, is described in WO02057287; WO2003062255; WO2003093290; WO2004000858; WO2004002999; WO2004003138; WO2008062206; WO2009067409; WO2010075517; WO2010075549; WO2010081082; WO2010084115; WO2012092484; WO2012142093; WO2013096679; WO2014100498; WO2014209983; WO2015081297; WO2016069975; WO2016115222; and WO2016144918 the contents of which are hereby incorporated by reference for all purposes and the specific purposes identified herein.

In one particular implementation, the compound, or variations and permutations thereof, is described in WO2018041091 and WO2018127096 the contents of which are hereby incorporated by reference for all purposes and the specific purposes identified herein.

In one implementation, the RNA polymerase inhibitor compound is adefovir dipivoxil, (((2-(6-amino-9H-purin-9-yl)ethoxy)methyl)phosphonic acid).

In one particular implementation, the compound, or variations and permutations thereof, is described in US20050080053; WO2004106350 and WO2008056264 the contents of which are hereby incorporated by reference for all purposes and the specific purposes identified herein.

In one implementation, the RNA polymerase inhibitor compound is Ademetionine ((2S)-2-amino-4-((((2S,3S,4R,5R)-5-(6-amino-9H-purin-9-yl)-3,4-dihydroxytetrahydrofuran-2-yl)methyl)(methyl)sulfonio)butanoate).

In one particular implementation, the compound, or variations and permutations thereof, is described in WO2004003138 the contents of which are hereby incorporated by reference for all purposes and the specific purposes identified herein.

In one implementation, the RNA polymerase inhibitor compound is Adenosine or Adenosine triphosphate.

In one particular implementation, the compound, or variations and permutations thereof, is described in WO2013096679; WO2015081297; WO2015161137; WO2016115222 and WO2018013937 the contents of which are hereby incorporated by reference for all purposes and the specific purposes identified herein.

In one implementation, the RNA polymerase inhibitor compound is Alovudine (1-[(2R,4S,5R)-4-fluoro-5-(hydroxymethyl)oxolan-2-yl]-5-methylpyrimidine-2,4-dione).

In one particular implementation, the compound, or variations and permutations thereof, is described in CN110655546; US20130143835; WO02051425; WO02057287; WO2004000858; WO2008121634; WO2009067409; WO2012142085; WO2012142093; WO2013070887; WO2013096679; WO2014062596; WO2014078463; WO2014100505; WO2014209983; WO2015034420; WO2015081297; WO2015095419; WO2015120237; WO2016100569; and WO2016115222 the contents of which are hereby incorporated by reference for all purposes and the specific purposes identified herein.

In one implementation, the RNA polymerase inhibitor compound is Aspacytarabine (N4-(1-β-D-arabinofuranosyl-2-oxo-1,2-dihydropyrimidin-4-yl)-L-asparagine).

In one particular implementation, the compound, or variations and permutations thereof, is described in WO2003093290; WO2004002999; WO2004046159; WO2006021341; WO2008043704; WO2009067409; WO2013096679; WO2014209983; and WO2016115222 the contents of which are hereby incorporated by reference for all purposes and the specific purposes identified herein.

In one implementation, the RNA polymerase inhibitor compound is Azvudine (4-amino-1-((2R,3S,4R,5R)-5-azido-3-fluoro-4-hydroxy-5-(hydroxymethyl)tetrahydrofuran-2-yl)pyrimidin-2(1H)-one).

In one particular implementation, the compound, or variations and permutations thereof, is described in EP02166016; WO2003093290; WO2004046159; WO2006021341; WO2008043704; WO2009067409; WO2014209983; WO2014209983; and WO2016115222 the contents of which are hereby incorporated by reference for all purposes and the specific purposes identified herein.

In one implementation, the RNA polymerase inhibitor compound is Balapiravir ((2R,3S,4R,5R)-5-(4-amino-2-oxopyrimidin-1(2H)-yl)-2-azido-2-((isobutyryloxy)methyl) tetrahydrofuran-3,4-diyl bis(2-methylpropanoate)).

In one particular implementation, the compound, or variations and permutations thereof, is described in WO02057287; WO2004046159; WO2006021341; WO2007020193; WO2008043704; WO2008142055; WO2012142075; WO2012142093; WO2012154321; WO2014209983; and WO2016115222 the contents of which are hereby incorporated by reference for all purposes and the specific purposes identified herein.

In one implementation, the RNA polymerase inhibitor compound is Beclabuvir ((8S,10R)-19-cyclohexyl-N-(dimethylsulfamoyl)-5-methoxy-10-(3-methyl-3,8-diazabicyclo [3.2.1]octane-8-carbonyl)-12-azapentacyclo[10.7.0.02,7.08, 10.013,18]nonadeca-1(19),2(7),3,5,13(18),14,16-heptaene-15-carboxamide).

In one particular implementation, the compound, or variations and permutations thereof, is described in WO2007136982; WO2008111978; WO2008112473; WO2008112841; WO2008112848; WO2008112851; WO2008112863; WO2009067108; WO2009067392; WO2009067392; and WO2009067481 the contents of which are hereby incorporated by reference for all purposes and the specific purposes identified herein.

In one implementation, the RNA polymerase inhibitor compound is Brivudine (5-[(E)-2-bromoethenyl]-1-[(2R,4S, 5R)-4-hydroxy-5-(hydroxymethyl)oxolan-2-yl]-1,2,3,4-tetrahydropyrimidine-2,4-dione).

In one particular implementation, the compound, or variations and permutations thereof, is described in CN110655546; US20130143835; WO02051425; WO02057287; WO2004000858; WO2008121634; WO2009067409; WO2012142085; WO2012142093; WO2013070887; WO2013096679; WO2014062596; WO2014078463; WO2014100505; WO2014209983; WO2015034420; WO2015081297; WO2015081297; WO2015095419; WO2015120237; WO2016100569; and WO2016115222 the contents of which are hereby incorporated by reference for all purposes and the specific purposes identified herein.

In one implementation, the RNA polymerase inhibitor compound is Bucladesine ((2R,4aS,6R,7R,7aR)-6-(6-butyramido-9H-purin-9-yl)-2-hydroxy-2-oxidotetrahydro-4H-furo[3,2-d][1,3,2]dioxaphosphinin-7-yl butyrate).

In one particular implementation, the compound, or variations and permutations thereof, is described in WO2017223020; WO2018013937; and WO2018091542 the contents of which are hereby incorporated by reference for all purposes and the specific purposes identified herein.

In one implementation, the RNA polymerase inhibitor compound is Capecitabine (pentyl (1-((2R,3R,4S,5R)-3,4-dihydroxy-5-methyltetrahydrofuran-2-yl)-5-fluoro-2-oxo-1,2-dihydropyrimidin-4-yl)carbamate).

In one particular implementation, the compound, or variations and permutations thereof, is described in WO2004046159 the contents of which are hereby incorporated by reference for all purposes and the specific purposes identified herein.

In one implementation, the RNA polymerase inhibitor compound is Cidofovir ((S)-(((1-(4-amino-2-oxopyrimidin-1(2H)-yl)-3-hydroxypropan-2-yl)oxy)methyl)phosphonic acid).

In one particular implementation, the compound, or variations and permutations thereof, is described in WO2003087298; WO2004106350; WO2003087298 and WO2011130557 the contents of which are hereby incorporated by reference for all purposes and the specific purposes identified herein.

In one implementation, the RNA polymerase inhibitor compound is Citicoline (2-((((((2S,3R,4S,5S)-5-(4-amino-2-oxopyrimidin-1(2H)-yl)-3,4-dihydroxytetrahydrofuran-2-yl)methoxy)(hydroxy)phosphoryl)oxy)oxidophosphoryl)oxy)-N,N,N-trimethylethan-1-aminium). In one particular implementation, the compound, or variations and permutations thereof, is described in US20040229840; WO2008005542; WO2008082601; WO2012142085; WO2012142093; WO2013096679; WO2014062596; WO2014100505; WO2014209983; WO2015034420; WO2015081297; WO2015095419; WO2015161137; WO2016100569; WO2016115222 the contents of which are hereby incorporated by reference for all purposes and the specific purposes identified herein In one implementation, the RNA polymerase inhibitor compound is Cladribine ((2R,3S,5R)-5-(6-amino-2-chloro-9H-purin-9-yl)-2-(hydroxymethyl)tetrahydrofuran-3-ol)).

In one particular implementation, the compound, or variations and permutations thereof, is described in WO02057287; WO2003062255; WO2003093290; WO2004000858; WO2004002999; WO2004003138; WO2008062206; WO2009067409; WO2010075517; WO2010075549; WO2010081082; WO2010084115; WO2012092484; WO2012142093; WO2013070887; WO2013096679; WO2014209983; WO2015081297; WO2015120237; WO2016069975; WO2016115222; and WO2016144918 the contents of which are hereby incorporated by reference for all purposes and the specific purposes identified herein.

In one implementation, the RNA polymerase inhibitor compound is Clemizole (1-p-Chlorobenzyl-2-(1-pyrrolidinylmethyl)benzimidazole).

In one particular implementation, the compound, or variations and permutations thereof, is described in WO2009039246 and WO2010091409 the contents of which are hereby incorporated by reference for all purposes and the specific purposes identified herein.

In one implementation, the RNA polymerase inhibitor compound is Clevudine (1-((2S,3R,4S,5S)-3-fluoro-4-hydroxy-5-(hydroxymethyl)tetrahydrofuran-2-yl)-5-methylpyrimidine-2,4(1H,3H)-dione).

In one particular implementation, the compound, or variations and permutations thereof, is described in CN110655546; US20130143835; WO02051425; WO02057287; WO2004000858; WO2008121634; WO2009067409; WO2012142085; WO2012142093; WO2013009737; WO2013070887; WO2013096679; WO2014062596; WO2014078463; WO2014100505; WO2014209983; WO2015034420; WO2015081297; WO2015095419; WO2015120237; WO2016100569 and WO2016115222 the contents of which are hereby incorporated by reference for all purposes and the specific purposes identified herein.

In one implementation, the RNA polymerase inhibitor compound is Clofarabine ((2S,3S,4R,5R)-5-(6-amino-2-chloro-9H-purin-9-yl)-4-fluoro-2-(hydroxymethyl)tetrahydrofuran-3-ol).

In one particular implementation, the compound, or variations and permutations thereof, is described in WO02057287; WO2003062255; WO2003093290; WO2004000858; WO2004002999; WO2004003138; WO2008062206; WO2009067409; WO2010075517; WO2010075549; WO2010081082; WO2010084115; WO2012092484; WO2012142093; WO2013070887; WO2013096679; WO2014100498; WO2014209983; WO2015081297; WO2015120237; WO2016069975; WO2016115222; and WO2016144918 the contents of which are hereby incorporated by reference for all purposes and the specific purposes identified herein.

In one implementation, the RNA polymerase inhibitor compound is Cytarabine (2(1H)-Pyrimidinone, 4-amino-1-beta-D-arabinofuranosyl-).

In one particular implementation, the compound, or variations and permutations thereof, is described in US20040229840; WO02057287; WO2003062255; WO2003093290; WO2004000858; WO2004002999; WO2008121634; WO2009067409; WO2012142085; WO2013009737; WO2013070887; WO2013096679; WO2014062596; WO2014100505; WO2014209983; WO2015081297; WO2015095419; WO2015120237; WO2016069975; WO2016100569; and WO2016115222 the contents of which are hereby incorporated by reference for all purposes and the specific purposes identified herein.

In one implementation, the RNA polymerase inhibitor compound is cytarabine ocfosfate (2(1H)-Pyrimidinone, 4-amino-1-(5-O-(hydroxy(octadecyloxy)phosphinyl)-beta-D-arabinofuranosyl)-In one particular implementation, the compound, or variations and permutations thereof, is described in US20040229840; WO2008005542; WO2008082601; WO2012142085; WO2012142093; WO2013096679; WO2014062596; WO2014100505; WO2014209983; WO2015034420; WO2015081297; WO2015095419; WO2015161137; WO2016100569; and WO2016115222 the contents of which are hereby incorporated by reference for all purposes and the specific purposes identified herein.

In one implementation, the RNA polymerase inhibitor compound is Daclatasvir (Dimethyl N,N'-(biphenyl-4,4'-diylbis{1H-imidazole-5,2-diyl-((2S)-pyrrolidine-2,1-diyl)((1 S)-1-(1-methylethyl)-2-oxoethane-2,1-diyl)})dicarbamate).

In one particular implementation, the compound, or variations and permutations thereof, is described in WO2013173492 the contents of which are hereby incorporated by reference for all purposes and the specific purposes identified herein.

In one implementation, the RNA polymerase inhibitor compound is Dexelvucitabine (4-amino-5-fluoro-1-((2R,5S)-5-(hydroxymethyl)-2,5-dihydrofuran-2-yl)pyrimidin-2(1H)-one).

In one particular implementation, the compound, or variations and permutations thereof, is described in WO2019040418 the contents of which are hereby incorporated by reference for all purposes and the specific purposes identified herein.

In one implementation, the RNA polymerase inhibitor compound is Didanosine (9-[(2R,5S)-5-(hydroxymethyl)oxolan-2-yl]-3H-purin-6-one).

In one particular implementation, the compound, or variations and permutations thereof, is described in WO02057287; WO2003093290; WO2004000858; WO2008062206; WO2012088155; WO2012092484; WO2013070887; WO2013096679; WO2014100498; WO2014100505; WO2014209983; WO2015054465; WO2015081297; WO2015095419; WO2015120237; WO2015161137; WO2016115222; and WO2018031818 the contents of which are hereby incorporated by reference for all purposes and the specific purposes identified herein In one implementation, the RNA polymerase inhibitor compound is Doxifluridine (1-((2R,3R,4S,5R)-3,4-dihydroxy-5-methyltetrahydrofuran-2-yl)-5-fluoropyrimidine-2,4(1H,3H)-dione).

In one particular implementation, the compound, or variations and permutations thereof, is described in WO2008100447; WO2015081297 and WO2017106710 the contents of which are hereby incorporated by reference for all purposes and the specific purposes identified herein In one implementation, the RNA polymerase inhibitor compound is Elacytarabine (E)-((2R,3S,4S,5R)-5-(4-amino-2-oxopyrimidin-1(2H)-yl)-3,4-dihydroxytetrahydrofuran-2-yl)methyl octadec-9-enoate).

In one particular implementation, the compound, or variations and permutations thereof, is described in WO02057287; WO2004046159; WO2006021341; WO2008043704; and WO2014209983 the contents of which are hereby incorporated by reference for all purposes and the specific purposes identified herein.

In one implementation, the RNA polymerase inhibitor compound is ethynylcytidine (1-(3-C-Ethynyl-beta-D-ribopentofuranosyl)cytosine).

In one particular implementation, the compound, or variations and permutations thereof, is described in US20040229840; WO02057287; WO2003062255; WO2003093290; WO2004000858; WO2004002999; WO2008121634; WO2009067409; WO2012142085; WO2013009737; WO2013070887; WO2013096679; WO2014062596; WO2014100505; WO2014209983; WO2015081297; WO2015095419; WO2015120237; WO2016069975; WO2016100569; and WO2016115222 the contents of which are hereby incorporated by reference for all purposes and the specific purposes identified herein.

In one implementation, the RNA polymerase inhibitor compound is Etodolac ((RS)-2-(1,8-Diethyl-4,9-dihydro-3H-pyrano[3,4-b]indol-1-yl)acetic acid).

In one particular implementation, the compound, or variations and permutations thereof, is described in WO2013096679; WO2015081297; WO2015161137; WO2016115222; and WO2018013937 the contents of which are hereby incorporated by reference for all purposes and the specific purposes identified herein.

Fludarabine ((2R,3S,4S,5R)-2-(6-amino-2-fluoropurin-9-yl)-5-(hydroxymethyl)oxolane-3,4-diol).

In one particular implementation, the compound, or variations and permutations thereof, is described in WO2013096679; WO2015081297; WO2015161137; WO2016115222; WO2018013937 the contents of which are hereby incorporated by reference for all purposes and the specific purposes identified herein.

In one implementation, the RNA polymerase inhibitor compound is Fosalvudine ((R)-2-(decyloxy)-3-(dodecylthio)propyl (((2R,3S,5R)-3-fluoro-5-(5-methyl-2,4-dioxo-3,4-dihydropyrimidin-1(2H)-yl)tetrahydrofuran-2-yl)methyl) hydrogen phosphate).

In one particular implementation, the compound, or variations and permutations thereof, is described in CN110655546 the contents of which are hereby incorporated by reference for all purposes and the specific purposes identified herein.

In one implementation, the RNA polymerase inhibitor compound is fosfluridine tidoxil (2-(decyloxy)-3-(dodecylthio)propyl (((2R,3S,4R,5R)-5-(5-fluoro-2,4-dioxo-3,4-dihydropyrimidin-1(2H)-yl)-3,4-dihydroxytetrahydrofuran-2-yl)methyl) hydrogen phosphate).

In one particular implementation, the compound, or variations and permutations thereof, is described in CN110655546; WO2014100505; WO2015081297; and WO2015161137 the contents of which are hereby incorporated by reference for all purposes and the specific purposes identified herein.

In one implementation, the RNA polymerase inhibitor compound is Galidesivir ((2S,3S,4R,5R)-2-(4-amino-5H-pyrrolo[3,2-d]pyrimidin-7-yl)-5-(hydroxymethyl)pyrrolidine-3,4-diol).

In one particular implementation, the compound, or variations and permutations thereof, is described in WO2006002231; WO2013158746; WO2014078778 the contents of which are hereby incorporated by reference for all purposes and the specific purposes identified herein.

In one implementation, the RNA polymerase inhibitor compound is gemcitabine elaidate ([(2R,3R,5R)-5-(4-amino-2-oxopyrimidin-1-yl)-4,4-difluoro-3-hydroxyoxolan-2-yl]methyl (E)-octadec-9-enoate) or gemcitabine hydrochloride.

In one particular implementation, the compound, or variations and permutations thereof, is described in WO2013096679 and WO2014209983 the contents of which are hereby incorporated by reference for all purposes and the specific purposes identified herein.

In one implementation, the RNA polymerase inhibitor compound is Gemcitabine hydrochloride (4-amino-1-[(2R,4R,5R)-3,3-difluoro-4-hydroxy-5-(hydroxymethyl)oxolan-2-yl]pyrimidin-2-one; hydrochloride).

In one particular implementation, the compound, or variations and permutations thereof, is described in US20040229840; WO02057287; WO2003062255; WO2003093290; WO2004000858; WO2004002999; WO2008121634; WO2009067409; WO2012142085; WO2013009737; WO2013070887; WO2013096679; WO2014062596; WO2014062596; WO2014100505; WO2014209983; WO2015081297; WO2015095419; WO2015120237; WO2016069975; WO2016100569; and WO2016115222 the contents of which are hereby incorporated by reference for all purposes and the specific purposes identified herein.

In one implementation, the RNA polymerase inhibitor compound is Golotimod, orilotimod or a compound described by the following formula (2R)-2-amino-5-[[(1S)-1-carboxy-2-(1H-indol-3-yl)ethyl]amino]-5-oxopentanoic acid.

In one particular implementation, the compound, or variations and permutations thereof, is described in WO2011153588 the contents of which are hereby incorporated by reference for all purposes and the specific purposes identified herein.

In one implementation, the RNA polymerase inhibitor compound is idoxuridine or APR (1-[(2R,4S,5R)-4-hydroxy-5-(hydroxymethyl)oxolan-2-yl]-5-iodopyrimidine-2,4-dione).

In one particular implementation, the compound, or variations and permutations thereof, is described in CN110655546; US20130143835; WO02057287; WO2004000858; WO2008121634; WO2009067409; WO2012142085; WO2012142093; WO2013070887; WO2013096679; WO2014062596; WO2014078463; WO2014100505; WO2014209983; WO2015034420; WO2015081297; WO2015095419; WO2015120237; WO2016100569 and WO2016115222 the contents of which are hereby incorporated by reference for all purposes and the specific purposes identified herein.

In one implementation, the RNA polymerase inhibitor compound is indoximod hydrochloride ((2R)-2-amino-3-(1-methylindol-3-yl)propanoic acid).

In one particular implementation, the compound, or variations and permutations thereof, is described in WO2011153588 the contents of which are hereby incorporated by reference for all purposes and the specific purposes identified herein.

In one implementation, the RNA polymerase inhibitor compound is Islatravir ((2R,3S,5R)-5-(6-amino-2-fluoropurin-9-yl)-2-ethynyl-2-(hydroxymethyl)oxolan-3-ol).

In one particular implementation, the compound, or variations and permutations thereof, is described in WO02057287; WO2003062255; WO2003093290; WO2004000858; WO2004002999; WO2004003138; WO2008062206; WO2009067409; WO2010075517; WO2010075549; WO2010081082; WO2010084115; WO2012092484; WO2012142093; WO2013070887; WO2013096679; WO2014100498; WO2014209983; WO2014209983; WO2015081297; WO2015120237; WO2016069975; WO2016115222 and WO2016144918 the contents of which are hereby incorporated by reference for all purposes and the specific purposes identified herein.

In one implementation, the RNA polymerase inhibitor compound is lagociclovir valactate (2-amino-9-[(2R,4S,5R)-4-fluoro-5-(hydroxymethyl)oxolan-2-yl]-1H-purin-6-one).

In one particular implementation, the compound, or variations and permutations thereof, is described in WO2004002999 and WO2018031818 the contents of which are hereby incorporated by reference for all purposes and the specific purposes identified herein In one implementation, the RNA polymerase inhibitor compound is Ledipasvir (methyl N-[(2S)-1-[(6S)-6-[5-[9,9-difluoro-7-[2-[(1R,3S,4S)-2-[(2S)-2-(methoxycarbonylamino)-3-methylbutanoyl]-2-azabicyclo[2.2.1]heptan-3-yl]-3H-benzimidazol-5-yl]fluoren-2-yl]-1H-imidazol-2-yl]-5-azaspiro[2.4]heptan-5-yl]-3-methyl-1-oxobutan-2-yl]carbamate).

In one particular implementation, the compound, or variations and permutations thereof, is described in WO2016141890 the contents of which are hereby incorporated by reference for all purposes and the specific purposes identified herein In one implementation, the RNA polymerase inhibitor compound is Lodenosine([(2S,4S,5R)-5-(6-aminopurin-9-yl)-4-fluorooxolan-2-yl]methanol).

In one particular implementation, the compound, or variations and permutations thereof, is described in WO02057287; WO2003093290; WO2004000858; WO2004002999; WO2004003138; WO2008062206; WO2009067409; WO2010075517; WO2010075549; WO2010084115; WO2012092484; WO2012142093; WO2013070887; WO2013096679; WO2014100498; WO2014209983; WO2015081297; WO2016069975; WO2016115222 and WO2016144918 the contents of which are hereby incorporated by reference for all purposes and the specific purposes identified herein In one implementation, the RNA polymerase inhibitor compound is Loxoribine (2-amino-9-[(2R,3R,4S,5R)-3,4-dihydroxy-5-(hydroxymethyl)oxolan-2-yl]-7-prop-2-enyl-1H-purine-6,8-dione).

In one particular implementation, the compound, or variations and permutations thereof, is described in WO02057287 and WO2008062206 the contents of which are hereby incorporated by reference for all purposes and the specific purposes identified herein In one implementation, the RNA polymerase inhibitor compound is Lumicitabine ([(2R,3R,4R,5R)-5-(4-amino-2-oxopyrimidin-1-yl)-2-(chloromethyl)-4-fluoro-3-(2-methylpropanoyloxy)oxolan-2-yl]methyl 2-methylpropanoate).

In one particular implementation, the compound, or variations and permutations thereof, is described in WO2004002999; WO2004046159; WO2008043704; WO2013096679; WO2014209983; WO2016069975 the contents of which are hereby incorporated by reference for all purposes and the specific purposes identified herein In one implementation, the RNA polymerase inhibitor compound is Mericitabine ([(2R,3R,4R,5R)-5-(4-amino-2-oxopyrimidin-1-yl)-4-fluoro-4-methyl-3-(2-methylpropanoyloxy)oxolan-2-yl]methyl 2-methylpropanoate).

In one particular implementation, the compound, or variations and permutations thereof, is described in WO2004002999; WO2004046159; WO2008043704; WO2013096679; WO2014209983 and WO2016069975 the contents of which are hereby incorporated by reference for all purposes and the specific purposes identified herein.

In one implementation, the RNA polymerase inhibitor compound is Metacavir ([(2S,5R)-5-(2-amino-6-methoxypurin-9-yl)oxolan-2-yl]methanol).

In one particular implementation, the compound, or variations and permutations thereof, is described in WO02057287; WO2003093290; WO2004000858; WO2004002999; WO2004003138; WO2008062206; WO2009067409; WO2010075517; WO2010075549; WO2010081082; WO2010084115; WO2012092484; WO2012142075; WO2012142093; WO2013070887; WO2013096679; WO2014100498; WO2014209983; WO2015081297; WO2015120237; WO2016069975; WO2016115222; and WO2016144918 the contents of which are hereby incorporated by reference for all purposes and the specific purposes identified herein.

In one implementation, the RNA polymerase inhibitor compound is Namodenoson ((2S,3S,4R,5R)-5-[2-chloro-6-[(3-iodophenyl)methylamino]purin-9-yl]-3,4-dihydroxy-N-methyloxolane-2-carboxamide).

In one particular implementation, the compound, or variations and permutations thereof, is described in WO2012092484 and WO2010081082 the contents of which are hereby incorporated by reference for all purposes and the specific purposes identified herein.

In one implementation, the RNA polymerase inhibitor compound is navuridine (1-[(2R,4S,5S)-4-azido-5-(hydroxymethyl)oxolan-2-yl]pyrimidine-2,4-dione).

In one particular implementation, the compound, or variations and permutations thereof, is described in CN110655546; US20130143835; WO02051425; WO02057287; WO2004000858; WO2008121634; WO2009067409; WO2011092158; WO2012142085; WO2012142093; WO2013070887; WO2013096679; WO2014062596; WO2014078463; WO2014100505; WO2014209983; WO2015034420; WO2015081297; WO2015095419; WO2015120237; WO2016100569; and WO2016115222 the contents of which are hereby incorporated by reference for all purposes and the specific purposes identified herein In one implementation, the RNA polymerase inhibitor compound is Nelarabine ((2R,3S,4S,5R)-2-(2-amino-6-methoxypurin-9-yl)-5-(hydroxymethyl)oxolane-3,4-diol).

In one particular implementation, the compound, or variations and permutations thereof, is described in WO02057287; WO2003062255; WO2003093290; WO2004000858; WO2004002999; WO2004003138; WO2008062206; WO2009067409; WO2010075517; WO2010075549; WO2010081082; WO2010084115; WO2012092484; WO2012092484; WO2012142075; WO2012142093; WO2013070887; WO2013096679; WO2014100498; WO2014209983; WO2015081297; WO2015120237; WO2016069975; WO2016115222; WO2016144918 the contents of which are hereby incorporated by reference for all purposes and the specific purposes identified herein.

In one implementation, the RNA polymerase inhibitor compound is Nitazoxanide ([2-[(5-nitro-1,3-thiazol-2-yl)carbamoyl]phenyl]acetate).

In one particular implementation, the compound, or variations and permutations thereof, is described in WO2009035788 the contents of which are hereby incorporated by reference for all purposes and the specific purposes identified herein.

In one implementation, the RNA polymerase inhibitor compound is one or more nucleoside analogs.

In one particular implementation, the compound, or variations and permutations thereof, is described in WO02057287; WO2003062255; WO2003093290; WO2004000858; WO2004002999; WO2004003138; WO2008062206; WO2009067409; WO2010075517; WO2010075549; WO2010081082; WO2010084115; WO2012092484; WO2012142093; WO2013070887; WO2013096679; WO2014100498; WO2014209983; WO2015081297; WO2015120237; WO2016069975; WO2016115222; and WO2016144918 the contents of which are hereby incorporated by reference for all purposes and the specific purposes identified herein.

In one implementation, the RNA polymerase inhibitor compound is Oxitriptan ((2S)-2-amino-3-(5-hydroxy-1H-indol-3-yl)propanoic acid).

In one particular implementation, the compound, or variations and permutations thereof, is described in WO2011153588 and WO2013187696 the contents of which are hereby incorporated by reference for all purposes and the specific purposes identified herein.

In one implementation, the RNA polymerase inhibitor compound is Phosphazid ([[(2S,3S,5R)-3-azido-5-(5-methyl-2,4-dioxopyrimidin-1-yl)oxolan-2-yl]methoxy-hydroxy-oxophosphanium).

In one particular implementation, the compound, or variations and permutations thereof, is described in WO2012088155 and WO2015081297 the contents of which are hereby incorporated by reference for all purposes and the specific purposes identified herein.

In one implementation, the RNA polymerase inhibitor compound is Piclidenoson ((2S,3S,4R,5R)-3,4-dihydroxy-5-[6-[(3-iodophenyl)methylamino]purin-9-yl]-N-methyl-oxolane-2-carboxamide).

In one particular implementation, the compound, or variations and permutations thereof, is described in WO2012092484 and WO2010081082 the contents of which are hereby incorporated by reference for all purposes and the specific purposes identified herein.

In one implementation, the RNA polymerase inhibitor compound is Pimodivir ((2S,3S)-3-[[5-fluoro-2-(5-fluoro-1H-pyrrolo[2,3-b]pyridin-3-yl)pyrimidin-4-yl]amino]bicyclo[2.2.2]octane-2-carboxylic acid).

In one particular implementation, the compound, or variations and permutations thereof, is described in WO2017097234; WO2018041091; WO2018157830 and WO2018157830 the contents of which are hereby incorporated by reference for all purposes and the specific purposes identified herein.

In one implementation, the RNA polymerase inhibitor compound is Raluridine (5-chloro-1-[(2R,4S,5R)-4-fluoro-5-(hydroxymethyl)oxolan-2-yl]pyrimidine-2,4-dione).

In one particular implementation, the compound, or variations and permutations thereof, is described in CN110655546; WO02051425; WO02057287; WO2004000858; WO2008121634; WO2009067409; WO2012142085; WO2012142093; WO2013070887; WO2013096679; WO2014078463; WO2014100505; WO2014209983; WO2015034420; WO2015081297; WO2015095419; WO2015120237; WO2016100569 and WO2016115222 the contents of which are hereby incorporated by reference for all purposes and the specific purposes identified herein.

In one implementation, the RNA polymerase inhibitor compound is Ravidasvir (methyl N-[(2S)-1-[(2S)-2-[5-[6-[2-[(2S)-1-[(2S)-2-(methoxycarbonylamino)-3-methylbutanoyl]pyrrolidin-2-yl]-3H-benzimidazol-5-yl]naphthalen-2-yl]-1H-imidazol-2-yl]pyrrolidin-1-yl]-3-methyl-1-oxobutan-2-yl]carbamate).

In one particular implementation, the compound, or variations and permutations thereof, is described in WO2011112429 and WO2016141890 the contents of which are hereby incorporated by reference for all purposes and the specific purposes identified herein.

In one implementation, the RNA polymerase inhibitor compound is Rociletinib (N-[3-[[2-[4-(4-acetylpiperazin-1-yl)-2-methoxyanilino]-5-(trifluoromethyl)pyrimidin-4-yl]amino]phenyl]prop-2-enamide).

In one particular implementation, the compound, or variations and permutations thereof, is described in WO2012058125 the contents of which are hereby incorporated by reference for all purposes and the specific purposes identified herein.

In one implementation, the RNA polymerase inhibitor compound is Ropidoxuridine (1-[(2R,4S,5R)-4-hydroxy-5-(hydroxymethyl)oxolan-2-yl]-5-iodopyrimidin-2-one).

In one particular implementation, the compound, or variations and permutations thereof, is described in US20040229840; WO02057287; WO2003062255; WO2003093290; WO2004000858; WO2004002999; WO2009067409; WO2013070887; WO2013096679; WO2014062596; WO2014100505; WO2014209983; WO2015081297; WO2015095419; WO2015120237; WO2016069975; WO2016100569; WO2016115222 the contents of which are hereby incorporated by reference for all purposes and the specific purposes identified herein.

In one implementation, the RNA polymerase inhibitor compound is Sapacitabine (N-[1-[(2R,3S,4S,5R)-3-cyano-4-hydroxy-5-(hydroxymethyl)oxolan-2-yl]-2-oxopyrimidin-4-yl]hexadecanamide).

In one particular implementation, the compound, or variations and permutations thereof, is described in WO2003093290; WO2004046159; WO2009067409; WO2013096679; WO2014209983 the contents of which are hereby incorporated by reference for all purposes and the specific purposes identified herein.

In one implementation, the RNA polymerase inhibitor compound is tenofovir ([(2R)-1-(6-aminopurin-9-yl)propan-2-yl]oxymethylphosphonic acid).

In one particular implementation, the compound, or variations and permutations thereof, is described in US20050080053; WO2004106350; WO2006137953; WO2008056264; and WO2011130557 the contents of which are hereby incorporated by reference for all purposes and the specific purposes identified herein.

In one implementation, the RNA polymerase inhibitor compound is, elodenoson ((2S,3S,4R,5R)-5-[6-(cyclopentylamino)purin-9-yl]-N-ethyl-3,4-dihydroxyoxolane-2-carboxamide).

In one particular implementation, the compound, or variations and permutations thereof, is described in WO2003093290 the contents of which are hereby incorporated by reference for all purposes and the specific purposes identified herein.

In one implementation, the RNA polymerase inhibitor compound is sorivudine (5-[(E)-2-bromoethenyl]-1-[(2R,3S,4S,5R)-3,4-dihydroxy-5-(hydroxymethyl)oxolan-2-yl]pyrimidine-2,4-dione).

In one particular implementation, the compound, or variations and permutations thereof, is described in CN110655546; US20130143835; WO02051425; WO02057287; WO2004000858; WO2008121634; WO2009067409; WO2012142085; WO2012142093; WO2013009737; WO2013070887; WO2013096679; WO2014062596; WO2014078463; WO2014100505; WO2014209983; WO2015034420; WO2015081297; WO2015081297; WO2015095419; WO2015120237; WO2016100569; WO2016115222 the contents of which are hereby incorporated by reference for all purposes and the specific purposes identified herein.

In one implementation, the RNA polymerase inhibitor compound is tecadenoson ((2R,3S,4R,5R)-2-(hydroxymethyl)-5-[6-[[(3R)-oxolan-3-yl]amino]purin-9-yl]oxolane-3,4-diol).

In one particular implementation, the compound, or variations and permutations thereof, is described in WO2003093290 the contents of which are hereby incorporated by reference for all purposes and the specific purposes identified herein.

In one implementation, the RNA polymerase inhibitor compound is Tegobuvir (5-[[6-[2,4-bis(trifluoromethyl)phenyl]pyridazin-3-yl]methyl]-2-(2-fluorophenyl)imidazo[4,5-c]pyridine).

In one particular implementation, the compound, or variations and permutations thereof, is described in WO2009111501 the contents of which are hereby incorporated by reference for all purposes and the specific purposes identified herein.

In one implementation, the RNA polymerase inhibitor compound is Telbivudine (1-[(2S,4R,5S)-4-hydroxy-5-(hydroxymethyl)oxolan-2-yl]-5-methylpyrimidine-2,4-dione).

In one particular implementation, the compound, or variations and permutations thereof, is described in CN110655546; US20130143835; WO02051425; WO02057287; WO2004000858; WO2008121634; WO2009067409; WO2012142085; WO2012142093; WO2013009737; WO2013070887; WO2013096679; WO2014062596; WO2014078463; WO2014100505; WO2014209983; WO2015034420; WO2015081297; WO2015081297; WO2015095419; WO2015120237; WO2016100569 and WO2016115222 the contents of which are hereby incorporated by reference for all purposes and the specific purposes identified herein.

In one implementation, the RNA polymerase inhibitor compound is Tenofovir ([(2R)-1-(6-aminopurin-9-yl)propan-2-yl]oxymethylphosphonic acid).

In one particular implementation, the compound, or US20050080053; WO2004106350; WO2008056264; and WO2011130557 variations and permutations thereof, is described in the contents of which are hereby incorporated by reference for all purposes and the specific purposes identified herein.

In one implementation, the RNA polymerase inhibitor compound is Tenofovir dipivoxil fumarate ([[[(2R)-1-(6-aminopurin-9-yl)propan-2-yl]oxymethyl-(propan-2-yloxycarbonyloxymethoxy)phosphoryl]oxymethyl propan-2-yl carbonate;(E)-but-2-enedioic acid) In one particular implementation, the compound, or variations and permutations thereof, is described in WO2008056264 and WO2011130557 the contents of which are hereby incorporated by reference for all purposes and the specific purposes identified herein.

In one implementation, the RNA polymerase inhibitor compound is one of tenofovir disoproxil orotate, tenofovir disoproxil aspartate, tenofovir disoproxil hemiedisylate or tenofovir.

In one particular implementation, the compound, or variations and permutations thereof, is described in US20050080053; WO2004106350; WO2008056264; WO2011130557, the contents of which are hereby incorporated by reference for all purposes and the specific purposes identified herein.

In one implementation, the RNA polymerase inhibitor compound is Tezacitabine (4-amino-1-[(2R,3E,4S,5R)-3-(fluoromethylidene)-4-hydroxy-5-(hydroxymethyl)oxolan-2-yl]pyrimidin-2-one).

In one particular implementation, the compound, or variations and permutations thereof, is described in WO2013096679 and WO2009067409 the contents of which are hereby incorporated by reference for all purposes and the specific purposes identified herein.

In one implementation, the RNA polymerase inhibitor compound is one or more thiazolides or others in the class of broad-spectrum antiviral drugs.

In one particular implementation, the compound, or variations and permutations thereof, is described in WO2009035788 the contents of which are hereby incorporated by reference for all purposes and the specific purposes identified herein.

In one implementation, the RNA polymerase inhibitor compound is Tocladesine ((4aR,6R,7R,7aS)-6-(6-amino-8-chloropurin-9-yl)-2-hydroxy-2-oxo-4a,6,7,7a-tetrahydro-4H-furo[3,2-d][1,3,2]dioxaphosphinin-7-ol).

In one particular implementation, the compound, or variations and permutations thereof, is described in WO2009152095; WO2012088155; WO2012142075; WO2015081297; and WO2016115222 the contents of which are hereby incorporated by reference for all purposes and the specific purposes identified herein.

In one implementation, the RNA polymerase inhibitor compound is uridine triacetate ([(2R,3R,4R,5R)-3,4-diacetyloxy-5-(2,4-dioxopyrimidin-1-yl)oxolan-2-yl]methyl acetate).

In one particular implementation, the compound, or variations and permutations thereof, is described in CN110655546; US20130143835; WO02051425; WO02057287; WO2004000858; WO2008121634; WO2009067409; WO2011092158; WO2012142085; WO2012142093; WO2013009737; WO2013070887; WO2013096679; WO2014062596; WO2014078463; WO2014100505; WO2014209983; WO2015034420; WO2015081297; WO2015095419; WO2015095419; WO2015120237; WO2016069975; WO2016100569 and WO2016115222 the contents of which are hereby incorporated by reference for all purposes and the specific purposes identified herein.

In one implementation, the RNA polymerase inhibitor compound is valopicitabine dihydrochloride ([(2R,3R,4R,5R)-5-(4-amino-2-oxopyrimidin-1-yl)-4-hydroxy-2-(hydroxymethyl)-4-methyloxolan-3-yl](2S)-2-amino-3-methylbutanoate; dihydrochloride).

In one particular implementation, the compound, or variations and permutations thereof, is described in EP02166016; WO2003093290; WO2004002999; WO2004046159; WO2006021341; WO2008043704; WO2009067409; WO2013096679; WO2014209983; WO2016115222 the contents of which are hereby incorporated by reference for all purposes and the specific purposes identified herein.

In one implementation, the RNA polymerase inhibitor compound is Valtorcitabine ([(2S,3R,5S)-5-(4-amino-2-oxopyrimidin-1-yl)-2-(hydroxymethyl)oxolan-3-yl](2S)-2-amino-3-methylbutanoate).

In one particular implementation, the compound, or variations and permutations thereof, is described in EP02166016; WO2003093290; WO2004002999; WO2004046159; WO2006021341; WO2008043704; WO2009067409; WO2009067409; WO2013096679; WO2014209983; WO2016115222 the contents of which are hereby incorporated by reference for all purposes and the specific purposes identified herein.

In one implementation, the RNA polymerase inhibitor compound is yimitasvir phosphate or another NS5A protein inhibitor.

In one particular implementation, the compound, or variations and permutations thereof, is described in WO2010132538 and WO2016141890 the contents of which are hereby incorporated by reference for all purposes and the specific purposes identified herein.

In one implementation, the RNA polymerase inhibitor compound is Zalcitabine (4-amino-1-[(2R,5S)-5-(hydroxymethyl)oxolan-2-yl]pyrimidin-2-one).

In one particular implementation, the compound, or variations and permutations thereof, is described in US20040229840; WO02057287; WO2003062255; WO2003093290; WO2004000858; WO2004002999; WO2008121634; WO2009067409; WO2012142085; WO2013009737; WO2013070887; WO2013096679; WO2014062596; WO2014100505; WO2014209983; WO2015081297; WO2015095419; WO2015120237; WO2016069975; WO2016100569; and WO2016115222 the contents of which are hereby incorporated by reference for all purposes and the specific purposes identified herein.

In one implementation, the RNA polymerase inhibitor compound is Zidovudine (1-[(2R,4S,5S)-4-azido-5-(hydroxymethyl)oxolan-2-yl]-5-methylpyrimidine-2,4-dione).

In one particular implementation, the compound, or variations and permutations thereof, is described in CN110655546; US20130143835; WO02051425; WO2004000858; WO2009067409; WO2011092158; WO2013096679; WO2014062596; WO2014078463; WO2014100505; WO2014209983; WO2015081297; WO2015081297; WO2015095419; WO2015120237; WO2016100569 and WO2016115222 the contents of which are hereby incorporated by reference for all purposes and the specific purposes identified herein.

In one implementation, the RNA polymerase inhibitor compound is A-837093(N-[3-[(4R)-1-hydroxy-4-methyl-4-(3-methylbutyl)-3-oxonaphthalen-2-yl]-1,1-dioxo-4H-1 lambda6,2,4-benzothiadiazin-7-yl]methanesulfonamide).

In one particular implementation, the compound, or variations and permutations thereof, is described in WO2015120237; WO2003000713; WO2016049415; WO2016115222 the contents of which are hereby incorporated by reference for all purposes and the specific purposes identified herein.

In one implementation, the RNA polymerase inhibitor compound is ABT-072 (N-[4-[(E)-2-[3-tert-butyl-5-(2,4-dioxopyrimidin-1-yl)-2-methoxyphenyl]ethenyl]phenyl] methanesulfonamide). In one particular implementation, the compound, or variations and permutations thereof, is described in WO2009039127; WO2009039135 and WO2015197028 the contents of which are hereby incorporated by reference for all purposes and the specific purposes identified herein In one implementation, the RNA polymerase inhibitor compound is ACH-3422 or other NS5B polymerase inhibitors.

In one particular implementation, the compound, or variations and permutations thereof, is described in US20130143835; WO2008121634; WO2010135569; WO2011039221; WO2012040126; WO2012142075; WO2012142085; WO2012142093; WO2013096679; WO2014062596; WO2014078463; WO2014100505; WO2015017713; WO2015034420; WO2015081297; WO2015120237; WO2015161137; WO2016049415; WO2016069975; WO2016069975; WO2016115222; WO2016145142; WO2017040766; and WO2017106710 the contents of which are hereby incorporated by reference for all purposes and the specific purposes identified herein.

In one implementation, the RNA polymerase inhibitor compound is BMS-986094 (2,2-dimethylpropyl (2S)-2-[[[[(2R,3R,4R,5R)-5-(2-amino-6-methoxypurin-9-yl)-3,4-dihydroxy-4-methyloxolan-2-yl]methoxy-naphthalen-1-yloxyphosphoryl]amino]propanoate).

In one particular implementation, the compound, or variations and permutations thereof, is described in WO2008062206; WO2010081082; WO2012040126; WO2012075140; WO2012092484; WO2012142075; WO2012142085; WO2012142093; WO2013070887; WO2014100505; WO2016049415; WO2016115222; WO2018013937; the contents of which are hereby incorporated by reference for all purposes and the specific purposes identified herein.

In one implementation, the RNA polymerase inhibitor compound is CX-5461 (2-(4-methyl-1,4-diazepan-1-yl)-N-[(5-methylpyrazin-2-yl)methyl]-5-oxo-[1,3]benzothiazolo[3,2-a][1,8]naphthyridine-6-carboxamide).

In one particular implementation, the compound, or variations and permutations thereof, is described in WO2009046383 the contents of which are hereby incorporated by reference for all purposes and the specific purposes identified herein.

In one particular implementation, the compound, or variations and permutations thereof, is described in WO2011103063; WO2011106929; and WO2016133948 the contents of which are hereby incorporated by reference for all purposes and the specific purposes identified herein In one implementation, the RNA polymerase inhibitor compound is GSK-2878175 (GSK-287817) (6-[(7-chloro-1-hydroxy-3H-2,1-benzoxaborol-5-yl)-methylsulfonylamino]-5-cyclopropyl-2-(4-fluorophenyl)-N-methyl-1-benzofuran-3-carboxamide).

In one particular implementation, the compound, or variations and permutations thereof, is described in WO2012067663 the contents of which are hereby incorporated by reference for all purposes and the specific purposes identified herein.

In one implementation, the RNA polymerase inhibitor compound is JTK-109 ([2-[4-[[2-(4-chlorophenyl)-5-(2-oxopyrrolidin-1-yl)phenyl]methoxy]-2-fluorophenyl]cyclohexyl]3H-benzimidazole-5-carboxylate).

In one particular implementation, the compound, or variations and permutations thereof, is described in WO2001047883 and WO2005014543 the contents of which are hereby incorporated by reference for all purposes and the specific purposes identified herein.

In one implementation, the RNA polymerase inhibitor compound is NB-1011, (methyl (2S)-2-[[[(2R,3S,5R)-5-[5-[(E)-2-bromoethenyl]-2,4-dioxopyrimidin-1-yl]-3-hydroxyoxolan-2-yl]methoxy-phenoxyphosphoryl]amino]propanoate) or other Thymidylate synthase inhibitor.

In one particular implementation, the compound, or variations and permutations thereof, is described in US20130143835; WO2008121634; WO2011039221; WO2012040126; WO2012142075; WO2012142085; WO2012142093; WO2013096679; WO2014062596; WO2014078463; WO2014100505; WO2015017713; WO2015034420; WO2015081297; WO2015120237; WO2015161137; WO2016049415; WO2016069975; WO2016115222; WO2016145142; WO2017040766; and WO2017106710 the contents of which are hereby incorporated by reference for all purposes and the specific purposes identified herein.

In one implementation, the RNA polymerase inhibitor compound is NUC-7738 (benzyl (2R)-2-[[[(2R,4S,5S)-5-(6-aminopurin-9-yl)-4-hydroxyoxolan-2-yl]methoxy-phenoxyphosphoryl]amino]propanoate).

In one particular implementation, the compound, or variations and permutations thereof, is described in WO2012142075 the contents of which are hereby incorporated by reference for all purposes and the specific purposes identified herein.

In one particular implementation, the compound, or variations and permutations thereof, is described in WO2012058125 and WO2013163466 the contents of which are hereby incorporated by reference for all purposes and the specific purposes identified herein.

In one implementation, the RNA polymerase inhibitor compound is UR-1505 (2-hydroxy-4-(2,2,3,3,3-pentafluoropropoxy)benzoic acid).

In one particular implementation, the compound, or variations and permutations thereof, is described in WO2000006529 the contents of which are hereby incorporated by reference for all purposes and the specific purposes identified herein.

In one implementation, the RNA polymerase inhibitor compound is VX-759 (3-[(4-methylcyclohexanecarbonyl)-propan-2-ylamino]-5-phenylthiophene-2-carboxylic acid).

In one particular implementation, the compound, or variations and permutations thereof, is described in WO02100851; WO2004052885; WO2006072347; WO2006119646 the contents of which are hereby incorporated by reference for all purposes and the specific purposes identified herein.

In one implementation, the RNA polymerase inhibitor compound is Adafosbuvir (propan-2-yl (2S)-2-[[[(2S,3S,4R,5R)-5-(2,4-dioxopyrimidin-1-yl)-2-fluoro-3,4-dihydroxy-4-methyloxolan-2-yl]methoxy-phenoxyphosphoryl]amino]propanoate).

In one particular implementation, the compound, or variations and permutations thereof, is described in US20130143835; WO2008121634; WO2010135569; WO2011039221; WO2012040126; WO2012142075; WO2012142085; WO2012142093; WO2013096679; WO2014062596; WO2014078463; WO2014078463; WO2014100505; WO2015017713; WO2015034420; WO2015081297; WO2015120237; WO2015161137; WO2016049415; WO2016069975; WO2016115222; WO2016145142; WO2017040766; WO2017106710 the contents of which are hereby incorporated by reference for all purposes and the specific purposes identified herein.

In one implementation, the RNA polymerase inhibitor compound is Boceprevir ((1R,2S,5S)—N-(4-amino-1-cyclobutyl-3,4-dioxobutan-2-yl)-3-[(2S)-2-(tert-butylcarbamoylamino)-3,3-dimethylbutanoyl]-6,6-dimethyl-3-azabicyclo[3.1.0]hexane-2-carboxamide).

In one particular implementation, the compound, or variations and permutations thereof, is described in WO2012018534 the contents of which are hereby incorporated by reference for all purposes and the specific purposes identified herein.

In one implementation, the RNA polymerase inhibitor compound is Ciluprevir ((1S,4R,6S,7Z,14S,18R)-14-(cyclopentyloxycarbonylamino)-18-[7-methoxy-2-[2-(propan-2-ylamino)-1,3-thiazol-4-yl]quinolin-4-yl]oxy-2,15-dioxo-3,16-diazatricyclo[14.3.0.04,6]nonadec-7-ene-4-carboxylic acid).

In one particular implementation, the compound, or variations and permutations thereof, is described in WO2009005676 the contents of which are hereby incorporated by reference for all purposes and the specific purposes identified herein.

In one implementation, the RNA polymerase inhibitor compound is Dasabuvir (N-[6-[3-tert-butyl-5-(2,4-dioxopyrimidin-1-yl)-2-methoxyphenyl]naphthalen-2-yl]methanesulfonamide).

In one particular implementation, the compound, or variations and permutations thereof, is described in WO2009039134; WO2015197028 and WO2009039127 the contents of which are hereby incorporated by reference for all purposes and the specific purposes identified herein In one implementation, the RNA polymerase inhibitor compound is Faldaprevir ((1R,2S)-1-[[(2S,4R)-4-[8-bromo-7-methoxy-2-[2-(2-methylpropanoylamino)-1,3-thiazol-4-yl]quinolin-4-yl]oxy-1-[(2S)-2-(cyclopentyloxycarbonylamino)-3,3-dimethylbutanoyl]pyrrolidine-2-carbonyl]amino]-2-ethenylcyclopropane-1-carboxylic acid).

In one particular implementation, the compound, or variations and permutations thereof, is described in WO2009005676 the contents of which are hereby incorporated by reference for all purposes and the specific purposes identified herein.

In one implementation, the RNA polymerase inhibitor compound is Filibuvir (2R)-2-cyclopentyl-2-[2-(2,6-diethylpyridin-4-yl)ethyl]-5-[(5,7-dimethyl-[1,2,4]triazolo[1,5-a] pyrimidin-2-yl)methyl]-4-hydroxy-3H-pyran-6-one).

In one particular implementation, the compound, or variations and permutations thereof, is described in WO2006018725 the contents of which are hereby incorporated by reference for all purposes and the specific purposes identified herein.

In one implementation, the RNA polymerase inhibitor compound is fosgemcitabine palabenamide (benzyl (2S)-2-[[[(2R,3R,5R)-5-(4-amino-2-oxopyrimidin-1-yl)-4,4-difluoro-3-hydroxyoxolan-2-yl]methoxy-phenoxyphosphoryl] amino]propanoate).

In one particular implementation, the compound, or variations and permutations thereof, is described in WO2015120237; WO2003000713; WO2016049415; and WO2016115222 the contents of which are hereby incorporated by reference for all purposes and the specific purposes identified herein.

In one implementation, the RNA polymerase inhibitor compound is fosifloxuridine nafalbenamide (benzyl (2S)-2-[[[(2R,3S,5R)-5-(5-fluoro-2,4-dioxopyrimidin-1-yl)-3-hydroxyoxolan-2-yl]methoxy-naphthalen-1-yloxyphosphoryl] amino]propanoate).

In one particular implementation, the compound, or variations and permutations thereof, is described in WO2016115222; WO2016049415; WO2012142075 the contents of which are hereby incorporated by reference for all purposes and the specific purposes identified herein.

In one implementation, the RNA polymerase inhibitor compound is Nesbuvir (-5-cyclopropyl-2-(4-fluorophenyl)-6-[2-hydroxyethyl(methylsulfonyl)amino]-N-methyl-1-benzofuran-3-carboxamide).

In one particular implementation, the compound, or variations and permutations thereof, is described in WO2004041201; WO2009137493; WO2009137500; WO2012067663; and WO2016154241 the contents of which are hereby incorporated by reference for all purposes and the specific purposes identified herein.

In one implementation, the RNA polymerase inhibitor compound is one or more of aspirin, acetylsalicylic acid (phosphatidylcholine-associated acetylsalicylic acid lysine acetylsalicylate.

In one particular implementation, the compound, or variations and permutations thereof, is described in WO2000006529 the contents of which are hereby incorporated by reference for all purposes and the specific purposes identified herein.

In one implementation, the RNA polymerase inhibitor compound is Remdesivir (2-ethylbutyl (2S)-2-[[[(2R,3S,4R,5R)-5-(4-aminopyrrolo[2,1-f][1,2,4]triazin-7-yl)-5-cyano-3,4-dihydroxyoxolan-2-yl]methoxy-phenoxyphosphoryl] amino]propanoate).

In one particular implementation, the compound, or variations and permutations thereof, is described in WO2009132123; WO2011035231; WO2012142075; WO2014059901; WO2016069975; and WO2019053696 the contents of which are hereby incorporated by reference for all purposes and the specific purposes identified herein.

In one implementation, the RNA polymerase inhibitor compound is SETROBUVIR (N-[3-[(1R,2S,7R,8S)-3-[(4-fluorophenyl)methyl]-6-hydroxy-4-oxo-3-azatricyclo[6.2.1.02,7]undec-5-en-5-yl]-1,1-dioxo-4H-1 lambda6,2,4-benzothiadiazin-7-yl]methanesulfonamide).

In one particular implementation, the compound, or variations and permutations thereof, is described in US20080292588; WO2008124450; WO2009152166; WO2010042830; and WO2012158271 the contents of which are hereby incorporated by reference for all purposes and the specific purposes identified herein.

In one implementation, the RNA polymerase inhibitor compound is sofosbuvir (propan-2-yl (2S)-2-[[[(2R,3R,4R,5R)-5-(2,4-dioxopyrimidin-1-yl)-4-fluoro-3-hydroxy-4-methyloxolan-2-yl]methoxy-phenoxyphosphoryl]amino] propanoate).

In one particular implementation, the compound, or variations and permutations thereof, is described in US20130143835; WO2008121634; WO2010135569; WO2011039221; WO2012040126; WO2012142075; WO2012142085; WO2012142093; WO2013096679; WO2014062596; WO2014078463; WO2014100505; WO2015017713; WO2015034420; WO2015081297; WO2015120237; WO2015161137; WO2016049415; WO2016069975; WO2016115222; WO2016145142; WO2017040766; and WO2017106710 the contents of which are hereby incorporated by reference for all purposes and the specific purposes identified herein.

In one implementation, the RNA polymerase inhibitor compound is triflusal, triflusal (enteric-coated, thromboembolism), Myungin or 2-acetyloxy-4-(trifluoromethyl)benzoic acid.

In one particular implementation, the compound, or variations and permutations thereof, is described in WO2000006529 the contents of which are hereby incorporated by reference for all purposes and the specific purposes identified herein. In one implementation, the RNA polymerase inhibitor compound is Uprifosbuvir (propan-2-yl (2R)-2-[[[(2R,3R,4R,5R)-4-chloro-5-(2,4-dioxopyrimidin-1-yl)-3-hydroxy-4-methyloxolan-2-yl]methoxy-phenoxyphosphoryl]amino]propanoate).

In one particular implementation, the compound, or variations and permutations thereof, is described in US20130143835; WO2008121634; WO2010135569; WO2011039221; WO2012040126; WO2012142075; WO2012142085; WO2012142085; WO2012142093; WO2012142093; WO2013096679; WO2013096679; WO2014062596; WO2014078463; WO2014100505; WO2015017713; WO2015034420; WO2015081297; WO2015120237; WO2016049415; WO2016069975; WO2016115222; WO2016145142; WO2017040766; and WO2017106710 the contents of which are hereby incorporated by reference for all purposes and the specific purposes identified herein.

In one implementation, the RNA polymerase inhibitor compound is Vedroprevir (1R,2R)-1-[[(2S,4R)-1-[(2S)-2-[[(1R,5S)-3-bicyclo[3.1.0]hexanyl]oxycarbonylamino]-3,3-dimethylbutanoyl]-4-[8-chloro-7-(2-morpholin-4-ylethoxy)-2-[2-(propan-2-ylamino)-1,3-thiazol-4-yl] quinolin-4-yl]oxypyrrolidine-2-carbonyl]amino]-2-ethylcyclopropane-1-carboxylic acid).

In one particular implementation, the compound, or variations and permutations thereof, is described in WO2009005676 the contents of which are hereby incorporated by reference for all purposes and the specific purposes identified herein.

In one implementation, the RNA polymerase inhibitor compound is Velaresol (5-(2-formyl-3-hydroxyphenoxy) pentanoic acid).

In one particular implementation, the compound, or variations and permutations thereof, is described in WO2000006529 the contents of which are hereby incorporated by reference for all purposes and the specific purposes identified herein.

In one implementation, the RNA polymerase inhibitor compound is Velpatasvir (methyl N-[(1R)-2-[(2S,4S)-2-[5-

[6-[(2S,5S)-1-[(2S)-2-(methoxycarbonylamino)-3-methylbutanoyl]-5-methylpyrrolidin-2-yl]-21-oxa-5,7-diazapentacyclo[11.8.0.03,11.04,8.014,19]henicosa-1(13),2,4(8),5,9,11,14(19),15,17-nonaen-17-yl]-1H-imidazol-2-yl]-4-(methoxymethyl)pyrrolidin-1-yl]-2-oxo-1-phenylethyl] carbamate).

In one particular implementation, the compound, or variations and permutations thereof, is described in WO2013173488 the contents of which are hereby incorporated by reference for all purposes and the specific purposes identified herein.

In one implementation, the RNA polymerase inhibitor compound is zaleplon (N-[3-(3-cyanopyrazolo[1,5-a]pyrimidin-7-yl)phenyl]-N-ethylacetamide).

In one particular implementation, the compound, or variations and permutations thereof, is described in WO2003101993 the contents of which are hereby incorporated by reference for all purposes and the specific purposes identified herein.

In one implementation, the RNA polymerase inhibitor compound is dl-PHPB 2-(1-hydroxypentyl)-benzoate.

In one particular implementation, the compound, or variations and permutations thereof, is described in WO2000006529 the contents of which are hereby incorporated by reference for all purposes and the specific purposes identified herein.

Methods of Treatment

In certain embodiments, the compositions and methods of the present disclosure are useful for the prevention and/or treatment of symptoms of SARS-CoV-19 infections. In certain embodiments, the compositions and methods of the present disclosure are useful for the prevention and/or treatment of acute inflammatory responses. In certain embodiments, the compositions and methods of the present disclosure are useful for the prevention and/or treatment of acute inflammatory responses, e.g., cytokine storms that are associates with a coronavirus infection.

The present disclosure is based on the discovery that RNA polymerase inhibitors may have therapeutic utility in the treatment of coronavirus symptoms, in particular in preventing viral replication in critical patients with coronavirus infections, in particular SARS-CoV-19. RNA polymerase inhibitors or reduce viral replication if viruses, thereby decreasing the viral load suffered by an infected patient.

Thus, in some embodiments, RNA polymerase inhibitors may prevent onset of severe SARS-CoV-19 symptoms. For example, RNA polymerase inhibitors may reduce or eliminate the viral load in patients with SARS-CoV-19 pneumonia and prevent or ameliorate progress thereof. Successful intervention with RNA polymerase inhibitors may reduce life-threatening complications of SARS-CoV-19, including severe respiratory symptoms that often necessitate further medical intervention such as mechanical intervention.

Thus, in some embodiments, the present disclosure relates to a method of treating or alleviating at least one symptom of a coronavirus infection in a subject, by administering to the subject a therapeutically effective amount of RNA polymerase inhibitors. In some embodiments, the subject is a human.

In some embodiments, the symptom is fever. In other embodiments, the symptom is cough. In other embodiments, the symptom is dry cough. In other embodiments, the symptom is tiredness. In other embodiments, the symptom is sore throat. In other embodiments, the symptom is diarrhea. In other embodiments, the symptom is conjunctivitis. In other embodiments, the symptom is headache. In other embodiments, the symptom is loss of taste. In other embodiments, the symptom is loss of smell. In other embodiments, the symptom is a rash. In other embodiments, the symptom is difficulty breathing. In other embodiments, the symptom is shortness of breath. In other embodiments, the symptom is chest pain. In other embodiments, the symptom is chest pressure. In other embodiments, the symptom is Acute Respiratory Distress Syndrome (ARDS). In other embodiments, the symptom is organ failure. In other embodiments, the symptom is multiple organ failure. In other embodiments, the symptom is any combination of the foregoing.

In some embodiments, the present disclosure relates to a method of treating an acute condition in a subject infected with a coronavirus, the method comprising the step of administering to the subject a therapeutically effective amount of RNA polymerase inhibitors. In some embodiments, the condition comprises a high viral load. In some embodiments, the subject is a human.

In some embodiments, the present disclosure relates to a method of reducing or arresting viral load in a subject infected with a coronavirus, the method comprising the step of administering to the subject a therapeutically effective amount of a RNA polymerase inhibitors. In some embodiments, the subject is a human.

Viral load can be measured by any viral diagnostic equipment or technique known in the art. A wide variety of samples can be used for virological testing. Such samples include, but are not limited to, upper respiratory swabs (nasopharyngeal swabs, nasopharyngeal wash/aspirate, oropharyngeal swabs, saliva) and lower respiratory specimens (sputum, bronchoalveolar lavage, lung tissue), as well as stool, rectal swabs, blood, skin, urine, semen, faeces, cerebrospinal fluid, tissue (e.g., biopsies), and the like. Techniques for measuring viral load include, but are not limited to, nucleic acid amplification-based tests (NATs) or non-nucleic acid-based tests. Examples of NATs include, but are not limited to, PCR (polymerase chain reaction), reverse transcription polymerase chain reaction (RT-PCR), and nucleic acid sequence-based amplification (NASBA). Viral load is typically reported as copies the virus in a milliliter (mL) of blood. Changes in viral load are usually reported as a log change (in powers of 10). For example, a three-log increase in viral load (3 log 10) is an increase of 103 or 1,000 times the previously reported level, while a drop from 500,000 to 500 copies would be a three-log-drop.

In one embodiment, the subject is infected with a coronavirus. In some embodiments, the coronavirus is selected from the group consisting of 229E (alpha coronavirus), NL63 (alpha coronavirus), OC43 (beta coronavirus), HKU1 (beta coronavirus), MERS-CoV (beta coronavirus that causes Middle East Respiratory Syndrome, or MERS), SARS-CoV (the beta coronavirus that causes severe acute respiratory syndrome, or SARS) SARS-CoV-2 (the novel coronavirus that causes coronavirus disease 2019, or COVID-19, also referred to herein as SARS-Covid-19). In some embodiments, the coronavirus is a severe acute respiratory syndrome coronavirus (SARS-CoV). In some embodiments, the coronavirus is a novel virus 2019-nCoV (SARS-CoV-19). In some embodiments, the coronavirus is a Middle East respiratory syndrome coronavirus (MERS-CoV). In one preferred embodiment, the coronavirus is SARS-CoV-19.

Pharmaceutical Compositions

The present disclosure thus provides pharmaceutical compositions comprising RNA polymerase inhibitors and a pharmaceutically acceptable carrier. The compounds of the present disclosure can be formulated as pharmaceutical compositions and administered to a mammalian host, such as a human patient, in a variety of forms adapted to the chosen route of administration.

Routes of administration include, but are not limited to oral, topical, mucosal, nasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural and sublingual administration.

As used herein, the term "administering" generally refers to any and all means of introducing compounds described herein to the host subject. Compounds described herein may be administered in unit dosage forms and/or compositions containing one or more pharmaceutically-acceptable carriers, adjuvants, diluents, excipients, and/or vehicles, and combinations thereof.

As used herein, the terms "composition" generally refers to any product comprising more than one ingredient, including the compounds described herein. It is to be understood that the compositions described herein may be prepared from compounds described herein or from salts, solutions, hydrates, solvates, and other forms of the compounds described herein. It is appreciated that the compositions may be prepared from various amorphous, non-amorphous, partially crystalline, crystalline, and/or other morphological forms of the compounds described herein, and the compositions may be prepared from various hydrates and/or solvates of the compounds described herein. Accordingly, such pharmaceutical compositions that recite compounds described herein include each of, or any combination of, or individual forms of, the various morphological forms and/or solvate or hydrate forms of the compounds described herein.

In some embodiments, the RNA polymerase inhibitors may be systemically (e.g., orally) administered in combination with a pharmaceutically acceptable vehicle such as an inert diluent or an assimilable edible carrier. For oral therapeutic administration, the active compound may be combined with one or more excipients and used in the form of ingestible tablets, buccal tablets, sublingual tablets, troches, capsules, elixirs, suspensions, syrups, wafers, and the like. The percentage of the compositions and preparations may vary and may be between about 1 to about 99% weight of the active ingredient(s) and excipients such as, but not limited to a binder, a filler, a diluent, a disintegrating agent, a lubricant, a surfactant, a sweetening agent; a flavoring agent, a colorant, a buffering agent, anti-oxidants, a preservative, chelating agents (e.g., ethylenediaminetetraacetic acid), and agents for the adjustment of tonicity such as sodium chloride.

Suitable binders include, but are not limited to, polyvinylpyrrolidone, copovidone, hydroxypropyl methylcellulose, starch, and gelatin.

Suitable fillers include, but are not limited to, sugars such as lactose, sucrose, mannitol or sorbitol and derivatives therefore (e.g. amino sugars), ethylcellulose, microcrystalline cellulose, and silicified microcrystalline cellulose.

Suitable diluents include, but are not limited to, dicalcium phosphate dihydrate, sugars, lactose, calcium phosphate, cellulose, kaolin, mannitol, sodium chloride, and dry starch.

Suitable disintegrants include, but are not limited to, pregelatinized starch, crospovidone, crosslinked sodium carboxymethyl cellulose and combinations thereof.

Suitable lubricants include, but are not limited to, sodium stearyl fumarate, stearic acid, polyethylene glycol or stearates, such as magnesium stearate.

Suitable surfactants or emulsifiers include, but are not limited to, polyvinyl alcohol (PVA), polysorbate, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil.

Suitable flavoring agents and sweeteners include, but are not limited to, sweeteners such as sucralose and synthetic flavor oils and flavoring aromatics, natural oils, extracts from plants, leaves, flowers, and fruits, and combinations thereof. Exemplary flavoring agents include cinnamon oils, oil of wintergreen, peppermint oils, clover oil, hay oil, anise oil, *eucalyptus*, vanilla, citrus oil such as lemon oil, orange oil, grape and grapefruit oil, and fruit essences including apple, peach, pear, strawberry, raspberry, cherry, plum, pineapple, and apricot.

Suitable colorants include, but are not limited to, alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide.

Suitable buffering or pH adjusting agent include, but are not limited to, acidic buffering agents such as short chain fatty acids, citric acid, acetic acid, hydrochloric acid, sulfuric acid and fumaric acid; and basic buffering agents such as tris, sodium carbonate, sodium bicarbonate, sodium hydroxide, potassium hydroxide and magnesium hydroxide.

Suitable tonicity enhancing agents include, but are not limited to, ionic and non-ionic agents such as, alkali metal or alkaline earth metal halides, urea, glycerol, sorbitol, mannitol, propylene glycol, and dextrose.

Suitable wetting agents include, but are not limited to, glycerin, cetyl alcohol, and glycerol monostearate.

Suitable preservatives include, but are not limited to, benzalkonium chloride, benzoxonium chloride, thiomersal, phenylmercuric nitrate, phenylmercuric acetate, phenylmercuric borate, methylparaben, propylparaben, chlorobutanol, benzyl alcohol, phenyl alcohol, chlorohexidine, and polyhexamethylene biguanide.

Suitable antioxidants include, but are not limited to, sorbic acid, ascorbic acid, ascorbate, glycine, α-tocopherol, butylated hydroxyanisole (BHA), and butylated hydroxytoluene (BHT).

The RNA polymerase inhibitors of the present disclosure may also be administered via infusion or injection (e.g., using needle (including microneedle) injectors and/or needle-free injectors). Solutions of the active composition can be aqueous, optionally mixed with a nontoxic surfactant and/or may contain carriers or excipients such as salts, carbohydrates and buffering agents (preferably at a pH of from 3 to 9), and, for some applications, they may be more suitably formulated as a sterile non-aqueous solution or as a dried form to be used in conjunction with a suitable vehicle such as sterile, pyrogen-free water or phosphate-buffered saline. For example, dispersions can be prepared in glycerol, liquid polyethylene glycols, triacetin, and mixtures thereof and in oils. The preparations may further contain a preservative to prevent the growth of microorganisms.

The pharmaceutical compositions may be formulated for parenteral administration (e.g., subcutaneous, intravenous, intra-arterial, transdermal, intraperitoneal or intramuscular injection) and may include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Water is a preferred carrier when the pharmaceutical composition is administered intravenously. Saline solutions and aqueous dextrose and glycerol solutions can also be employed as liquid carriers, particularly for injectable solutions. Oils such as petroleum, animal, vegetable, or synthetic oils and soaps such as fatty alkali metal, ammonium, and triethanolamine salts, and suitable detergents may also be used for parenteral administration. Further, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. Suitable preservatives include e.g. sodium benzoate, benzoic acid, and sorbic acid. Suitable antioxidants include e.g. sulfites, ascorbic acid and L-tocopherol.

The preparation of parenteral compounds/compositions under sterile conditions, for example, by lyophilization, may readily be accomplished using standard pharmaceutical techniques well known to those skilled in the art.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. In one embodiment, the compositions are administered by the oral or nasal respiratory route for local or systemic effect. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, orally or nasally, from devices that deliver the formulation in an appropriate manner.

In yet another embodiment, the composition is prepared for topical administration, e.g. as an ointment, a gel, a drop, a patch or a cream. For topical administration to body surfaces using, for example, creams, gels, drops, ointments and the like, the compounds of the present disclosure can be prepared and applied in a physiologically acceptable diluent with or without a pharmaceutical carrier. Adjuvants for topical or gel base forms may include, for example, sodium carboxymethylcellulose, polyacrylates, polyoxyethylene-polyoxypropylene-block polymers, polyethylene glycol, wood wax alcohols, isostearic acid, cetyl alcohol, stearyl alcohol, white petrolatum, polysorbate 60, sorbitan monostearate, glycerin, xanthan gum, water, benzyl alcohol, methylparaben, and propylparaben. Additional additives may be selected from the group consisting of waxes, soaps, sorbitan esters, fatty acids, fatty acid esters, fatty acid oils, borates, cresol, chlorocresol, cellulose, methylcellulose, hydroxypropylcellulose, acacia, and the like. Examples of suitable topical dosage forms may be found in e.g., Tarun Garg, Goutam Rath & Amit K. Goyal (2015) Comprehensive review on additives of topical dosage forms for drug delivery, Drug Delivery, 22:8, 969-987, the contents of which are hereby incorporated by reference in their entirety.

Alternative formulations include nasal sprays, liposomal formulations, slow-release formulations, pumps delivering the drugs into the body (including mechanical or osmotic pumps) controlled-release formulations and the like, as are known in the art.

Doses

As used herein, the term "therapeutically effective dose" means (unless specifically stated otherwise) a quantity of a compound which, when administered either one time or over the course of a treatment cycle affects the health, wellbeing or mortality of a subject (e.g., delays the onset of and/or reduces the severity of one or more of the symptoms associated with a coronavirus, e.g., SARS-Covid-19.

A RNA polymerase inhibitors described herein can be present in a composition in an amount of about 0.001 mg, about 0.005 mg, about 0.01 mg, about 0.02 mg, about 0.03 mg, about 0.04 mg, about 0.05 mg, about 0.06 mg, about 0.07 mg, about 0.08 mg, about 0.09 mg about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 0.5 mg, about 10 mg, about 10.5 mg, about 11 mg, about 12 mg, about 12.5 mg, about 13 mg, about 13.5 mg, about 14 mg, about 14.5 g, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg.

RNA polymerase inhibitors described herein described herein can be present in a composition in a range of from about 0.1 mg to about 100 mg; 0.1 mg to about 75 mg; from about 0.1 mg to about 50 mg; from about 0.1 mg to about 25 mg; from about 0.1 mg to about 10 mg; 0.1 mg to about 7.5 mg, 0.1 mg to about 5 mg; 0.1 mg to about 2.5 mg; from about 0.1 mg to about 1 mg; from about 0.5 mg to about 100 mg; from about 0.5 mg to about 75 mg; from about 0.5 mg to about 50 mg; from about 0.5 mg to about 25 mg; from about 0.5 mg to about 10 mg; from about 0.5 mg to about 5 mg, from about 0.5 mg to about 2.5 mg; from about 0.5 mg to about 1 mg; from about 1 mg to about 100 mg; from about 1 mg to about 75 mg; from about 0.1 mg to about 50 mg; from about 0.1 mg to about 25 mg; from about 0.1 mg to about 10 mg; from about 0.1 mg to about 5 mg; from about 0.1 mg to about 2.5 mg; from about 0.1 mg to about 1 mg.

Dosing Regimens

The compounds described herein can be administered by any dosing schedule or dosing regimen as applicable to the patient and/or the condition being treated. Administration can be once a day (q.d.), twice a day (b.i.d.), thrice a day (t.i.d.), once a week, twice a week, three times a week, once every 2 weeks, once every three weeks, or once a month twice, and the like.

In some embodiments, the RNA polymerase inhibitor is administered for a period of at least one day. In other embodiments, the RNA polymerase inhibitor is administered for a period of at least 2 days. In other embodiments, the RNA polymerase inhibitor is administered for a period of at least 3 days. In other embodiments, the RNA polymerase inhibitor is administered for a period of at least 4 days. In other embodiments, the RNA polymerase inhibitor is administered for a period of at least 5 days. In other embodiments, the RNA polymerase inhibitor is administered for a period of at least 6 days. In other embodiments, the RNA polymerase inhibitor is administered for a period of at least 7 days. In other embodiments, the RNA polymerase inhibitor is administered for a period of at least 10 days. In other embodiments, the RNA polymerase inhibitor is administered for a period of at least 14 days. In other embodiments, the RNA polymerase inhibitor is administered for a period of at least one month. In some embodiments, the RNA polymerase inhibitor is administered chronically for as long as the treatment is needed.

The present subject matter described herein will be illustrated more specifically by the following non-limiting examples, it being understood that changes and variations can be made therein without deviating from the scope and the spirit of the disclosure as hereinafter claimed. It is also understood that various theories as to why the disclosure works are not intended to be limiting.

The foregoing description of the specific embodiments will so fully reveal the general nature of the disclosure that others can, by applying knowledge within the skill of the relevant art(s) (including the contents of the documents cited and incorporated by reference herein for all purposes), readily modify and/or adapt for various applications such specific embodiments, without undue experimentation, without departing from the general concept of the present disclosure. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

While various embodiments of the present disclosure have been described above, it should be understood that they have been presented by way of examples, and not limitation. It would be apparent to one skilled in the relevant art(s) that various changes in form and detail could be made therein without departing from the spirit and scope of the disclosure. Thus, the present disclosure should not be limited by any of the above-described exemplary embodiments but should be defined only in accordance with the following claims and their equivalents.

What is claimed:

1. A method of treating or alleviating at least one symptom of a coronavirus infection in a subject, the method comprising the step of administering to the subject a therapeutically effective amount of an RNA polymerase inhibitor, wherein the symptom is selected from the group consisting of fever, cough, tiredness, sore throat, diarrhea, conjunctivitis, headache, loss of taste, loss of smell, rash, difficulty breathing, shortness of breath, chest pain, chest pressure, Acute Respiratory Distress Syndrome (ARDS) and organ failure.

2. The method of claim 1, wherein the symptom is an acute inflammatory condition in a subject infected with a coronavirus.

3. The method according to claim 2, wherein the inflammatory condition comprises a cytokine storm.

4. The method of claim 1, wherein the treating or alleviating includes reducing or arresting viral load in a subject infected with a coronavirus.

5. The method according to claim 1, wherein the coronavirus is selected from the group consisting of severe acute respiratory syndrome coronavirus (SARS-COV), novel virus 2019-nCOV (SARS-COV-19), and the Middle East respiratory syndrome coronavirus (MERS-COV).

6. The method according to claim 5, wherein the coronavirus is SARS-COV-19.

7. The method according to claim 1, wherein the RNA polymerase inhibitor is selected from the group consisting of:
   DFP-10917 ((2R,3S,4S,5R)-2-(4-amino-2-oxopyrimidin-1-yl)-4-hydroxy-5-(hydroxymethyl)oxolane-3-carbonitrile);
   1-[(2R,3R,4S,5R)-3,4-dihydroxy-5-(hydroxymethyl)oxolan-2-yl]pyrimidine-2,4-dione;
   ([(2R,3R,5R)-5-(4-amino-2-oxopyrimidin-1-yl)-4,4-difluoro-3-hydroxyoxolan-2-yl]methyl (E)-octadec-9-enoate); and
   (1-(3-C-Ethynyl-beta-D-ribo-pentofuranosyl) cytosine) or variations or combinations thereof.

8. A method of treating or alleviating at least one symptom of a coronavirus infection in a subject, the method comprising the step of administering to the subject a therapeutically effective amount of an RNA polymerase inhibitor, wherein the symptom is an acute inflammatory condition in a subject infected with a coronavirus and wherein the RNA polymerase inhibitor is selected from the group consisting of a compound of any one of Table 1-150.

9. The method according to claim 1, wherein the RNA polymerase inhibitor is administered according to a dosing regimen selected from the group consisting of once daily (q.d.), twice daily (b.i.d.) thrice daily (t.i.d.), once a week, twice a week, three times a week, once every 2 weeks, once every three weeks, or once a month.

10. A method of treating or alleviating at least one symptom of a coronavirus infection in a subject, the method comprising the step of administering to the subject a therapeutically effective amount of an RNA polymerase inhibitor, wherein the symptom is an acute inflammatory condition in a subject infected with a coronavirus and wherein the RNA polymerase inhibitor is administered in a pharmaceutical composition, wherein the composition further comprises at least one pharmaceutically acceptable excipient.

11. The method according to claim 10, wherein the RNA polymerase inhibitor is administered in a form selected from the group consisting of a solution, a suspension, a syrup, an emulsion, a dispersion, a tablet, a pill, a capsule, a pellet, granules, a powder, an ointment, an elixir, a wafer, coated or uncoated beads, a lozenge, a sachet, a cachet, a depot system, a patch, an aerosol, an oil, an ointment, a suppository, a gel, and a cream.

12. The method according to claim 10, wherein the pharmaceutical composition is formulated for oral, topical, mucosal, intranasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural, sublingual oral, intranasal, intravenous, intraarterial, intrathecal, vaginal, rectal or subcutaneous administration.

13. The method according to claim 1, wherein the RNA polymerase inhibitor is administered in an amount of about 0.001 mg, about 0.005 mg, about 0.01 mg, about 0.02 mg, about 0.03 mg, about 0.04 mg, about 0.05 mg, about 0.06 mg, about 0.07 mg, about 0.08 mg, about 0.09 mg about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 0.5 mg, about 10 mg, about 10.5 mg, about 11 mg, about 12 mg, about 12.5 mg, about 13 mg, about 13.5 mg, about 14 mg, about 14.5 g, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, and about 100 mg.

14. The method according to claim 1, wherein the RNA polymerase inhibitor is present in a composition in a range of from about 0.1 mg to about 100 mg; 0.1 mg to about 75 mg; from about 0.1 mg to about 50 mg; from about 0.1 mg to about 25 mg; from about 0.1 mg to about 10 mg; 0.1 mg to about 7.5 mg, 0.1 mg to about 5 mg; 0.1 mg to about 2.5 mg; from about 0.1 mg to about 1 mg; from about 0.5 mg to about 100 mg; from about 0.5 mg to about 75 mg; from about 0.5 mg to about 50 mg; from about 0.5 mg to about 25 mg; from about 0.5 mg to about 10 mg; from about 0.5 mg to about 5 mg, from about 0.5 mg to about 2.5 mg; from about 0.5 mg to about 1 mg; from about 1 mg to about 100 mg; from about 1 mg to about 75 mg; from about 0.1 mg to about 50 mg; from about 0.1 mg to about 25 mg; from about 0.1 mg to about 10 mg; from about 0.1 mg to about 5 mg; from about 0.1 mg to about 2.5 mg; and from about 0.1 mg to about 1 mg.

15. The method according to claim 1, wherein the subject is a human.

* * * * *